(12) United States Patent
Butani et al.

(10) Patent No.: US 10,921,265 B2
(45) Date of Patent: Feb. 16, 2021

(54) SYSTEM AND METHOD FOR CABINET X-RAY SYSTEMS WITH NEAR-INFRARED OPTICAL SYSTEM

(71) Applicant: KUB Technologies Inc., Stratford, CT (US)

(72) Inventors: Vikram Butani, Stratford, CT (US); Chester Lowe, Stratford, CT (US); Vignesh Mandalapa-Bhoopathy, Stratford, CT (US); Edwin Maria-Selvaraj, Stratford, CT (US); Peter Yasutake, Stratford, CT (US)

(73) Assignee: KUB Techologies Inc., Stratford, CT (US)

( * ) Notice: Subject to any disclaimer, the term of this patent is extended or adjusted under 35 U.S.C. 154(b) by 0 days.

(21) Appl. No.: 16/856,264

(22) Filed: Apr. 23, 2020

(65) Prior Publication Data

US 2020/0340931 A1  Oct. 29, 2020

Related U.S. Application Data

(60) Provisional application No. 62/838,401, filed on Apr. 25, 2019, provisional application No. 62/837,986, filed on Apr. 24, 2019.

(51) Int. Cl.
| | | |
|---|---|---|
| G01N 23/04 | (2018.01) | |
| A61B 6/02 | (2006.01) | |
| G01N 23/00 | (2006.01) | |
| G01N 23/044 | (2018.01) | |
| G01N 21/359 | (2014.01) | |

(52) U.S. Cl.
CPC ......... *G01N 23/044* (2018.02); *G01N 21/359* (2013.01); *G01N 2223/408* (2013.01)

(58) Field of Classification Search
CPC ....... A61B 6/502; A61B 6/025; A61B 6/5217; A61B 6/4429; G01N 23/046; G01N 21/1702; G01N 21/31; G01N 21/4795; G01N 21/6456; G06T 2211/416; G06T 11/003
See application file for complete search history.

(56) References Cited

U.S. PATENT DOCUMENTS

| | | | |
|---|---|---|---|
| 9,138,193 B2 * | 9/2015 | Lowe | ............ A61B 6/502 |
| 10,492,747 B2 | 12/2019 | Divakaran et al. | |

(Continued)

*Primary Examiner* — Don K Wong
(74) *Attorney, Agent, or Firm* — Ziegler IP Law Group, LLC

(57) ABSTRACT

The present disclosure relates to the field of a cabinet x-ray incorporating an x-ray tube, an x-ray detector, and a near-infrared optical system mounted onto the cabinet or positioned within the cabinet, for the production of organic and non-organic images. The computing device receives video data from the near-infrared optical system and determines, based on the video data an optical image displaying the captured real-time image or display images adjacently i.e. Picture-In-Picture (PIP). In particular, the present disclosure also relates to a system and method with corresponding apparatus for capturing a near-infrared image simultaneously with the x-ray image allowing a cabinet x-ray unit to attain and optimize images utilizing near-infrared (NIR) fluorescence for sentinel lymph node (SLN) mapping in breast cancer patients to improve the Sentinel Lymph Node identification and procedure.

17 Claims, 16 Drawing Sheets

(56) References Cited

U.S. PATENT DOCUMENTS

| | | | |
|---|---|---|---|
| 2014/0336502 A1* | 11/2014 | Neelakanta | A61B 6/4417 600/424 |
| 2015/0131773 A1* | 5/2015 | Lowe | A61B 6/4429 378/5 |
| 2019/0187073 A1 | 6/2019 | Butani et al. | |

* cited by examiner

FRONT VIEW INTO CABINET
Door Open

Typical Example of an X-ray Cabinet System

View in Sample Chamber with Door Open with
X-ray source at position (14) Top Center

**Lateral View of X-Ray Source
Mounted to Swing Arm at position (14)

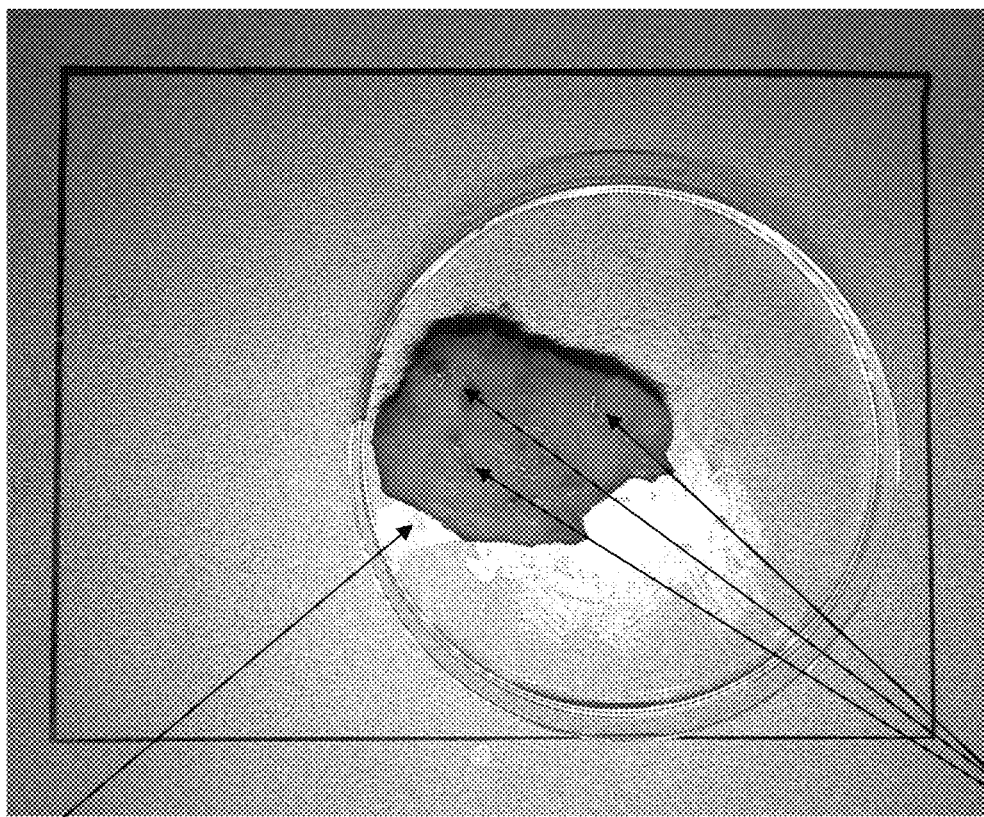
1000　　　　　Fig. 10A　　　　　1002
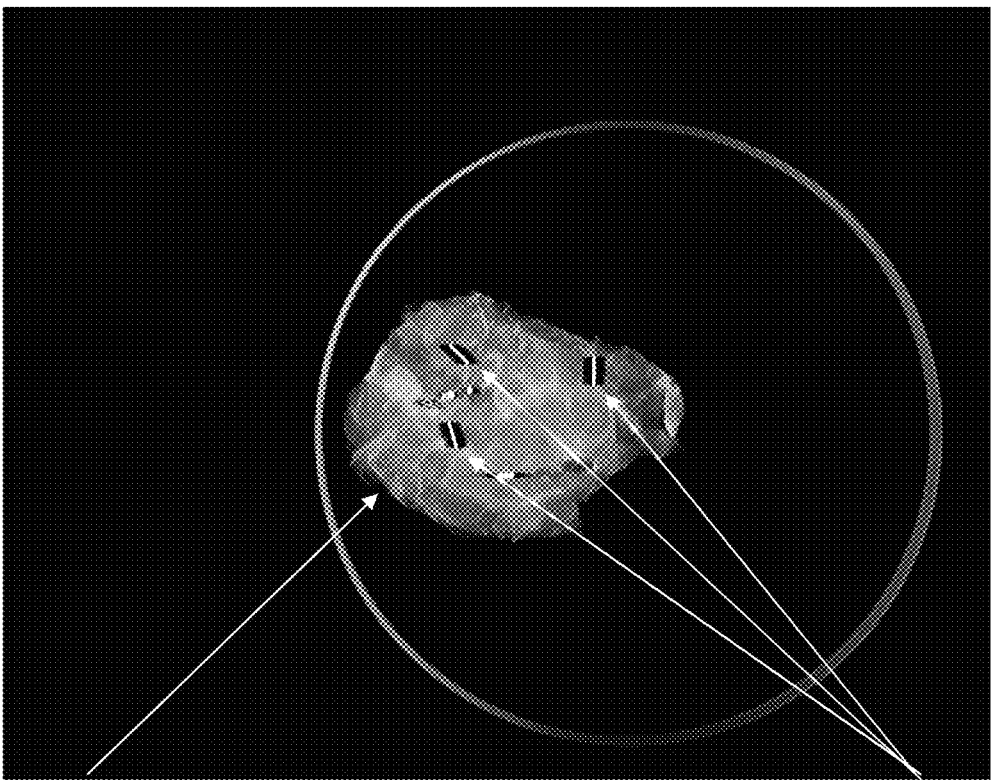
1000　　　　　Fig. 10B　　　　　1002

SYSTEM AND METHOD FOR CABINET X-RAY SYSTEMS WITH NEAR-INFRARED OPTICAL SYSTEM

CROSS-REFERENCE TO RELATED APPLICATIONS

This application claims priority to and the benefit of U.S. Provisional Patent Application Ser. No. 62/837,986 filed Apr. 24, 2019 and U.S. Provisional Patent Application Ser. No. 62/838,401 filed Apr. 25, 2019, the disclosures of which are incorporated herein by reference in their entirety.

BACKGROUND

Field of the Present Disclosure

The present disclosure relates to the field of a cabinet x-ray incorporating a system and method for incorporating a near-infrared (NIR) optical system onto it and taking a near-infrared image, and displaying the resulting images on the system monitor. NIR fluorescence imaging using indocyanine green (ICG) has the potential to improve the Sentinel lymph node SLN biopsy procedure by facilitating percutaneous and intraoperative identification of lymphatic channels and SLNs.

Background

Today, conventional breast specimen systems can gather a digital breast specimen radiogram and an optical image separately. In these systems, the radiograms and optical images of a tissue or bone specimen can be viewed separately for analysis.

With a unit incorporating a camera, the clinician can utilize the resultant photo or optical image to expeditiously visualize the specimen excised from the patient to confirm orientation of the excised sample saving time for both the patient on the treatment table and the clinician.

It would be advantageous in breast procedure rooms to allow the medical professional to operate the cabinet x-ray unit to analyze the excised breast tissue or specimen utilizing the unit to both x-ray and capture a near-infrared (NIR) as well as a visible light image of the sample for informational and/or diagnostic purposes.

The photo/captured NIR image may be displayed on the monitor either overlaid onto the resultant x-ray image of the sample or as a Picture-In-a-Picture (PIP) adjacent to the x-ray image of the sample.

Today, conventional breast specimen systems can gather a digital breast specimen radiogram separately. In these systems, the radiograms of a tissue or bone specimen are viewed separately for analysis.

With a unit incorporating a NIR camera, the clinician can utilize the resultant photo to expeditiously visualize the specimen excised from the patient to confirm orientation of the excised sample saving time for both the patient on the treatment table and the clinician.

Sentinel lymph node (SLN) biopsy is regarded as standard-of-care in staging the axilla in breast cancer patients with clinically negative lymph nodes. Three methods of mapping the sentinel lymph node are currently standard of care: 1) radioactive tracer alone, 2) blue dye, and 3) a combination of both. Prior to the use of NIR, the combination of both radioactive tracer and blue dye had reported the highest identification rates (>95%) and lowest false negative rates As a result of these issues, near-infrared (NIR) fluorescence (700-900 nm) imaging can be used for SLN mapping and has been tested in several cancer centers worldwide. NIR fluorescence imaging has several characteristics that are advantageous for the SLN procedure, which include a relatively high penetration into living tissue (up to 5 mm) and real-time, high-resolution optical guidance. Indocyanine green (ICG) is currently the only FDA and EMEA approved NIR fluorescent probe that can be used in clinical trials as a lymphatic tracer. This tracer has outperformed blue dye staining for SLN identification in several clinical trials.

A significant advantage of NIR imaging is that it can provide real-time guidance. However, to enable the surgeon to work under direct image guidance, navigation in relation to the surgical anatomy is obligatory. In contrast to most camera systems used worldwide, a system using a hands-free design NIR system (e.g., an NIR camera/detector and NIR light emitter) is capable of displaying NIR fluorescence signal simultaneously with surgical anatomy. Moreover, the real-time, high resolution images allow clear detection of fluorescent lymphatic channels, which has shown to be beneficial in the visualization of the lymphatic drainage pathway and position of the SLN.

Currently it is believed that there is not a system or method incorporating a NIR system incorporated with a cabinet x-ray system

SUMMARY

The present disclosure relates to the field of a cabinet x-ray incorporating an x-ray tube, an x-ray detector, and a Near-Infrared Optical system mounted onto the cabinet or therein for the production of organic and non-organic images. The computing device receives video data from the real-time camera and the x-ray detector and determines, based on the video data, an overlay of the captured x-ray image with the captured real-time image or display an adjacent image i.e. Picture-In-Picture (PIP). In particular, the present disclosure relates to a system and method with corresponding apparatus for capturing a NIR image from a NIR system mounted onto or a NIR system mounted within the cabinet x-ray unit (the latter including simultaneously obtaining the NIR images with the x-ray image) and allowing the user to attain and optimize images (for simultaneously obtained images from being mounted within the cabinet, with exact orientation) of the 2 images allowing the surgeon or user to visualize sentinel node mapping.

In another embodiment, the aspects of the present disclosure are directed to a cabinet x-ray and near-infrared (NIR) system for obtaining x-ray images and NIR images of a specimen. The cabinet x-ray and NIR image system includes a cabinet defining an interior chamber, a display, an x-ray system, an NIR system and a controller. The x-ray system includes an x-ray source, an x-ray detector and a specimen platform. The NIR image system is configured to capture an NIR image of the specimen and includes an NIR camera/detector and an NIR excitation light. The controller is configured to selectively energize the x-ray source to emit x-rays through the specimen to the x-ray detector, control the x-ray detector to collect a projection x-ray image of the specimen when the x-ray source is energized, selectively display the x-ray image on the display, control the NIR image system to capture and collect the NIR image of the specimen and selectively display the NIR image on the display.

In another embodiment, the aspects of the present disclosure are directed to a cabinet x-ray, near-infrared (NIR) and optical camera system for obtaining x-ray images, projection x-ray images, reconstructed tomosynthetic x-ray images, NIR images and optical images of a specimen. The cabinet x-ray and optical camera system includes a cabinet defining an interior chamber and an equipment enclosure, a display, an x-ray system, an optical camera, near-infrared (NIR) image system and a controller. The x-ray system includes an x-ray source positioned in the interior chamber, an x-ray detector positioned in the interior chamber, a specimen platform positioned in the interior chamber and which is a protective cover of and in physical contact with the x-ray detector and a motion control mechanism positioned in the interior chamber and configured for moving the x-ray source to or along a plurality of positions within the interior chamber relative to the specimen disposed on the specimen platform. The optical camera is positioned in the interior chamber and configured to capture an optical image of the specimen. The NIR image system is configured to capture an NIR image of the specimen and includes an NIR camera/detector and an NIR excitation light. The controller is positioned in the equipment enclosure and configured to selectively energize the x-ray source to emit x-rays through the specimen to the x-ray detector at selected positions of the x-ray source relative to the specimen such that the isocenter of the emitted x-rays at the selected positions is located at a surface of the x-ray detector, control the x-ray detector to collect projection x-ray images of the specimen when the x-ray source is energized at the selected positions, wherein one of the projection x-ray images is a two-dimensional x-ray image taken at standard imaging angle of approximately 0°, create a tomosynthetic x-ray image reconstructed from a collection of projection x-ray images, process the collection of the projection x-ray images in the controller into one or more reconstructed tomosynthetic x-ray images representing a volume of the specimen and relating to one or more image planes that are selectively the same or different from that of the two-dimensional x-ray image, control the optical camera to capture and collect the optical image of the specimen, control the NIR image system to capture and collect the NIR image of the specimen and selectively display the NIR image and at least one of the two-dimensional x-ray image, the one or more reconstructed tomosynthetic x-ray images and the optical image on the display.

In another embodiment, the aspects of the present disclosure are directed to a method for obtaining an x-ray image and a near-infrared (NIR) image of a specimen in a cabinet x-ray and NIR image system, processing and displaying the x-ray image and NIR image of the specimen. The cabinet x-ray and NIR image system includes a cabinet defining an interior chamber, a display, an x-ray system, an NIR image system and a controller. The x-ray system includes an x-ray source, an x-ray detector and a specimen platform. The NIR system configured to capture an NIR image of the specimen and includes an NIR camera/detector and an NIR excitation light. The controller is configured to selectively energize the x-ray source to emit x-rays through the specimen to the x-ray detector, control the x-ray detector to collect a projection x-ray image of the specimen when the x-ray source is energized, selectively display the x-ray image on the display, control the NIR system to capture and collect the NIR image of the specimen and selectively display the NIR image on the display. The method includes controlling the x-ray detector to collect an x-ray image of the specimen when the x-ray source is energized, controlling the NIR system to activate the NIR excitation light to emit to project NIR light toward the specimen and activate the NIR camera/detector to capture and collect the NIR image of the specimen and selectively displaying the NIR image and the x-ray image on the display.

BRIEF DESCRIPTION OF THE DRAWINGS

To further clarify the above and other advantages and features of the present disclosure, a more particular description of the disclosure will be rendered by reference to specific embodiments thereof that are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which:

FIGS. 10A and 10B—display an HD view and a radiographic image of a breast specimen utilizing exemplified embodiments of the present disclosure;

DETAILED DESCRIPTION

Figure 1:
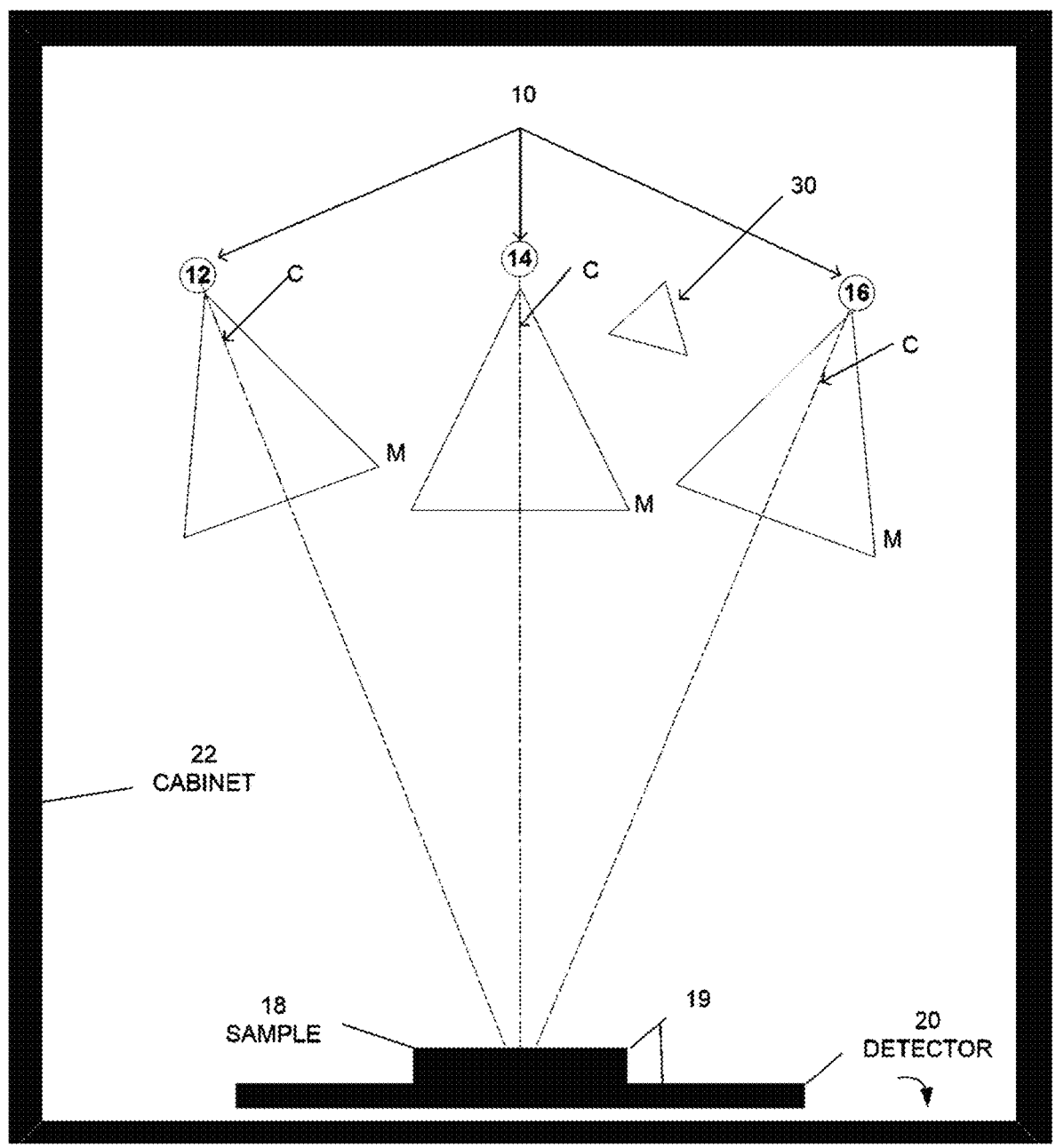
FIG. 1—Schematically illustrates a front view of an X-ray source, a specimen/sample, and a digital detector, where the X-ray source moves relative to the specimen for imaging the specimen at different angles, in one embodiment of a system incorporating aspects of the present disclosure.

In general, aspects of this disclosure include a device (cabinet x-ray system) utilizing a camera to capture an optical image (in black and white, gray scale or color, preferably color), preferably in real-time, of a sample or specimen and/or x-rayed to produce an x-ray image of the sample or specimen and utilizing a near-infrared (NIR) system to capture an NIR image (in black and white, gray scale or color, preferably color), preferably in real-time, of the sample or specimen, preferably with displaying the NIR image and at least one of the other images, preferably being at substantially or, preferably exactly, the same orientation in picture-in-picture or overlaying at least two of the images of the sample or specimen. The x-ray image can include a two-dimensional (2-D) x-ray image or a synthetic x-ray image assembled from more than one x-ray image (e.g., a tomosynthetic image). The NIR system can be positioned within or on the exterior of the cabinet housing the camera and x-ray systems.

NIR fluorescence imaging using indocyanine green (ICG) has the potential to improve the SLN procedure by facilitating percutaneous and intraoperative identification of lymphatic channels and SLNs.

The photo/captured camera optical image, preferably in real-time, may be displayed on the monitor either overlaid onto the resultant NIR image and/or the resultant x-ray image or synthetic x-ray image assembled from more than one x-ray image (e.g., a tomosynthetic image) of the sample or as back to back viewing on a monitor between at least any two of these images or a side-by-side or Picture-In-a-Picture (PIP) including displayed adjacent to the x-ray image or synthetic x-ray image of the sample. A device capturing both an x-ray image, an NIR image and an optical image, the latter two preferably in real-time, of the specimen facilitates confirmation and orientation for the clinician to verify margins and other specimen features are achieved by the professional after it is removed from a patient.

A preferred embodiment system would be to incorporate an HD (high-definition) optical camera into a cabinet x-ray unit allowing the system to capture an HD optical image and x-ray image of the specimen along with an NIR system ((e.g., an NIR camera/detector and NIR light emitter) either within the cabinet or mounted externally on the cabinet where the images so obtained can be displayed as disclosed herein.

The present disclosure and embodiments included therein can relate to specimen radiography but the disclosure is not isolated to specimen radiography but may be utilized, for example, for non-destructive testing, pathology as well as any radiographic analysis of organic and non-organic samples or specimens, requiring a cabinet x-ray system but is not limited to just an HD camera but to any camera fitting within the confines of the cabinet x-ray system as well as an NIR system ((e.g., an NIR camera/detector and NIR light emitter) either within the cabinet or mounted externally on the cabinet.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale. FIGS. 1-14 and 15A-15L depict various features and uses of embodiments of the present disclosure, which embodiments are generally directed to a system that can utilize an optical camera, preferably an HD or similar real-time camera, to capture an image of the specimen/sample concurrently with the acquisition of an x-ray image.

The systems and methods of embodiments of the present disclosure also address unmet needs by providing 2-D x-ray imaging and tomosynthesis apparatus and techniques that include optical imaging for imaging breast specimens that overcome the shortfall of the data received from two-dimensional and tomosynthesis imaging systems alone. The aspects of embodiments of the present disclosure also enable the use of tomosynthesis to efficiently provide accurate three-dimensional imaging of a specimen in which overlapping images having differing attenuation characteristics can be obtained by applying a three-dimensional reconstruction algorithm all in an x-ray cabinet system.

As used herein, the term "computer," "computer system", or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine-readable instructions, program or library of routines capable of executing on a computer or computer system including computer readable program code.

Digital breast specimen tomosynthesis is disclosed in U.S. Patent Publication No. 2015/0131773 (granted as U.S. Pat. No. 9,138,193), Lowe, et al., entitled "SPECIMEN RADIOGRAPHY WITH TOMOSYNTHESIS IN A CABINET" as it relates to the present subject matter of the title and related disclosure; U.S. Patent Publication No. 2019/0187073, entitled "SYSTEM AND METHOD FOR CABINET X-RAY SYSTEMS WITH CAMERA" as it relates to the present subject matter of the title and related disclosure; and U.S. Pat. No. 10,492,747, entitled "SYSTEM AND METHOD FOR EXTENDING AND RETRACTING A MOVEABLE ARM" as it relates to the present subject matter of the title and related disclosure, the disclosures of which are hereby incorporated by reference in their entirety.

The terms "camera" or "optical camera" refer to an instrument, including an optical instrument for capturing images in black and white, gray scale or color (preferably color) using reflected and/or emitted wavelengths of the electromagnetic spectrum, for example, visible light or fluorescent light, from an object, similar to a photograph or that which could be viewed by a human eye, using an electronic light-sensitive sensor array. These terms may include such instruments producing images in standard resolution or HD as well as a digital camera that can directly capture and store an image in computer-readable form using an array of electronic light-sensitive elements—typically semiconductor photo-sensors—that produce a light-intensity-dependent electronic signal in response to being illuminated.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale.

Specimen tomography is a three-dimensional specimen imaging system. It involves acquiring images of a sample at multiple viewpoints, typically over an arc or linear path. The three-dimensional image is constructed by the reconstruction of the multiple image data set.

One embodiment of a system 100 incorporating aspects of the present disclosure is illustrated in FIG. 1 The system 100 is totally enclosed or housed in an X-ray cabinet 22. In accordance with the aspects of the disclosed embodiments, the X-ray source 10 moves around the stationary sample, 18, typically, but not necessarily, in an arc. References 12, 14, and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam.

While the x-ray detector 20 (which can include a digital x-ray detector, a flat x-ray detector and a flat digital x-ray detector) may move or rotate, in accordance with one aspect of the present disclosure, the x-ray detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing image positions are utilized to form a digital tomosynthesis image.

In one embodiment, the aspects of the present disclosure limit the arc or linear travel of the x-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the x-ray detector 20 is stationary as is the sample 18. The sample 18 also referred to as the "object" or "imaging object" is disposed on or rests on the specimen platform 19 (which is a protective cover) or other surface of the x-ray detector 20.

In operation, source 10 is energized to emit an x-ray beam, generally throughout its travel along one or more of the paths or positions described above. The x-ray beam travels through the sample 18 to the x-ray detector 20 and the multiple images collected at varying angles are stored and then utilized for the tomosynthesis reconstruction. The X-ray source 10 may range from about 0 kVp to about 90 kVp, preferably a 50 kVp 1000 μa X-ray source.

Different embodiments of the present disclosure can utilize different ranges of motion of one or more of the X-ray source 10 and x-ray detector 20 as well as changing the angularity of one or both. The inventive aspects of the present disclosure differ from previous systems either the x-ray detector 20 and x-ray source 10 and/or the isocenter is above the sample and the isocenter is not at the detector surface. The isocenter of embodiments of the present disclosure is preferably positioned at the detector surface, for example, as shown in FIG. 1 where the reference "C" all converge for each of the positions 12, 14, 16 of the X-ray source 10 in FIG. 1. In accordance with the aspects of the present disclosure, in one embodiment, the X-ray source 10 is configured to move, as described herein, while the detector is configured to remain stationary or in a fixed position.

The detector 20 and associated electronics generate image data in digital form for each pixel at each of the angular positions, 12, 14, 16 of X-ray source 10 and translations positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10. The camera 30 represented in the figure may capture an optical image, preferably an HD image of the sample which can be stored with the radiographic images in computer 470.

Figure 2:
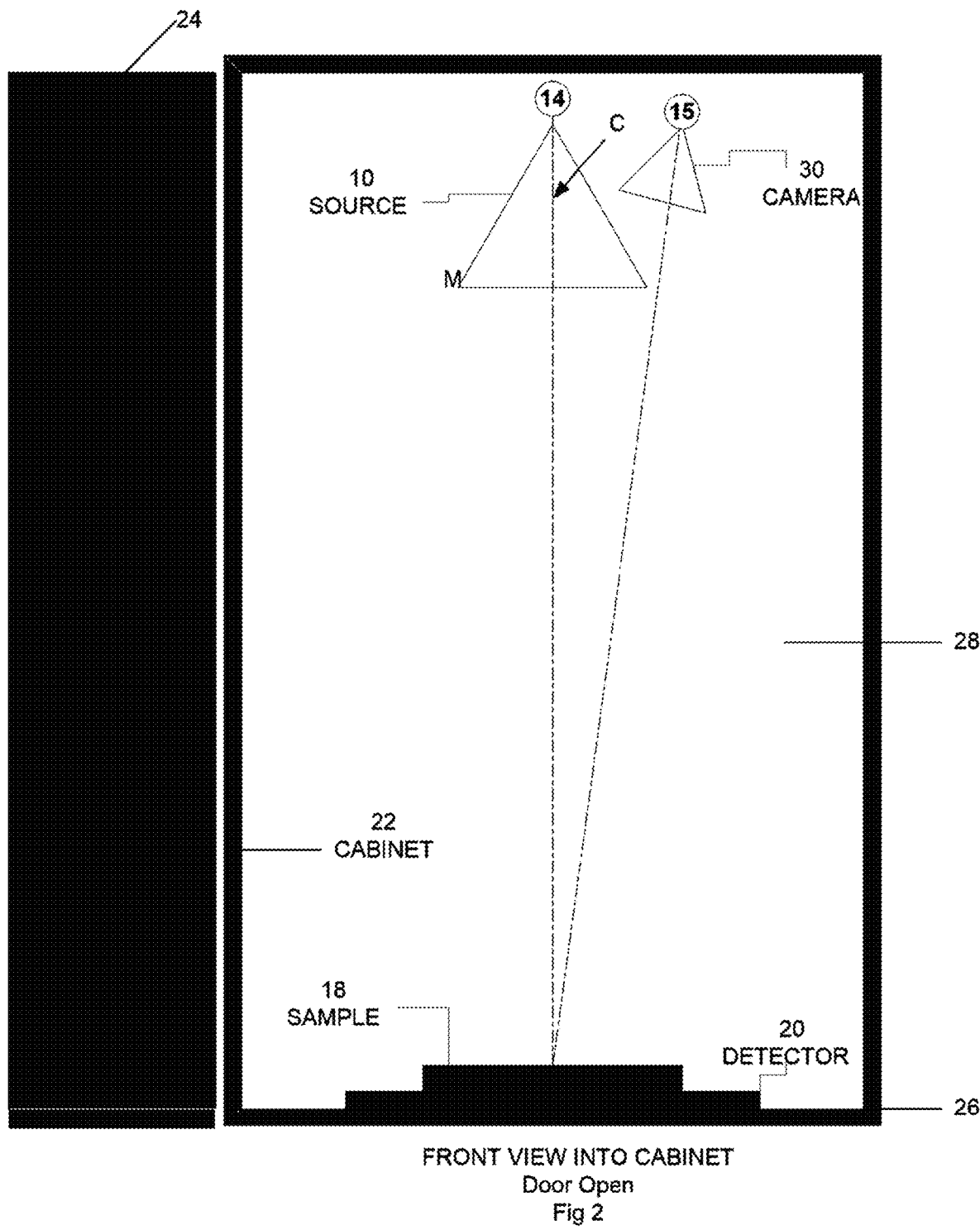
FIG. 2—Schematically illustrates an exemplary orientation of the X-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system preferably utilizing an AEC (Automatic Exposure Control) to ascertain the optimal setting to image the object or sample 18 being examined.

Figure 13:
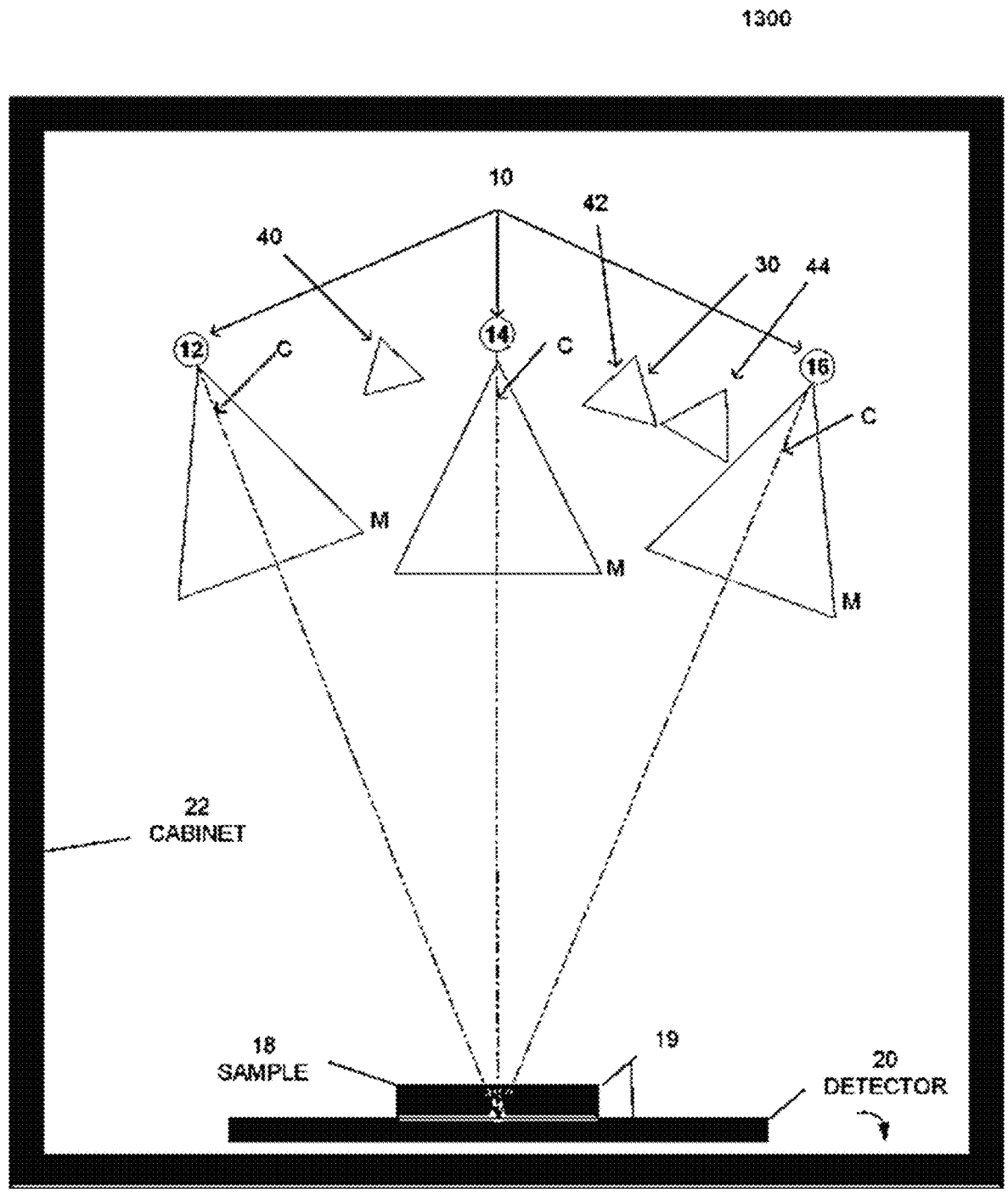
FIG. 13—Schematically illustrates a front view of an X-ray source, the NIR Infrared Source, a dual purpose camera, a specimen/sample, and a digital detector, where the X-ray source moves relative to the specimen for imaging the specimen at different angles, in one embodiment of a system incorporating aspects of the present disclosure internally.
Figure 14:
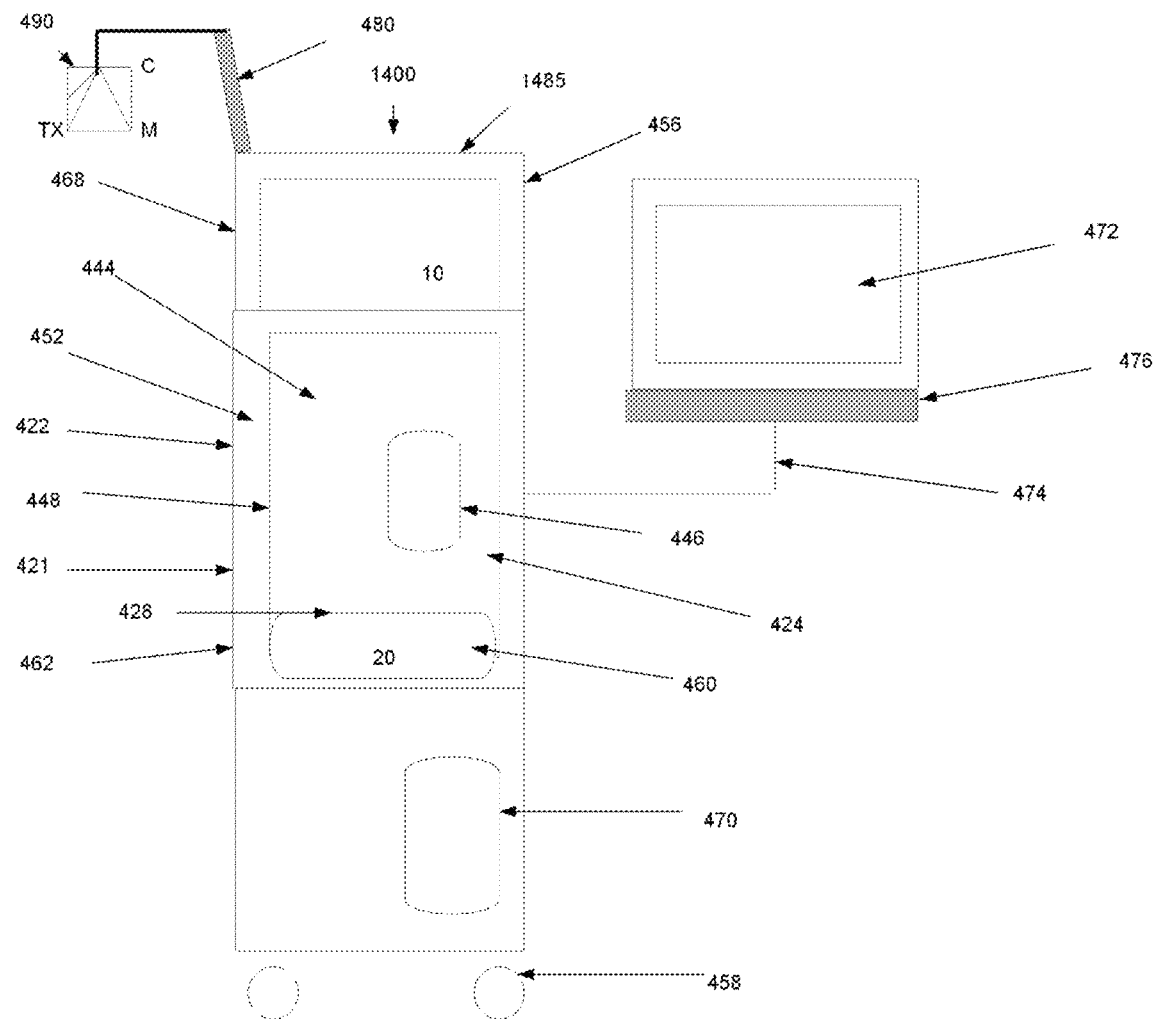
FIG. 14—Schematically illustrates an embodiment of the present disclosure whereas the NIR system from FIG. 11 is mounted outside of the X-ray Cabinet System shown in FIG. 4.

In one embodiment, the detector 20, X-ray source 10, and the swing arm 60 (FIG. 5) servo mechanism as well as the optical camera and NIR systems included in FIGS. 13 and 14 are controlled via a combination of one or more of software and hardware, such as non-transitory machine-readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
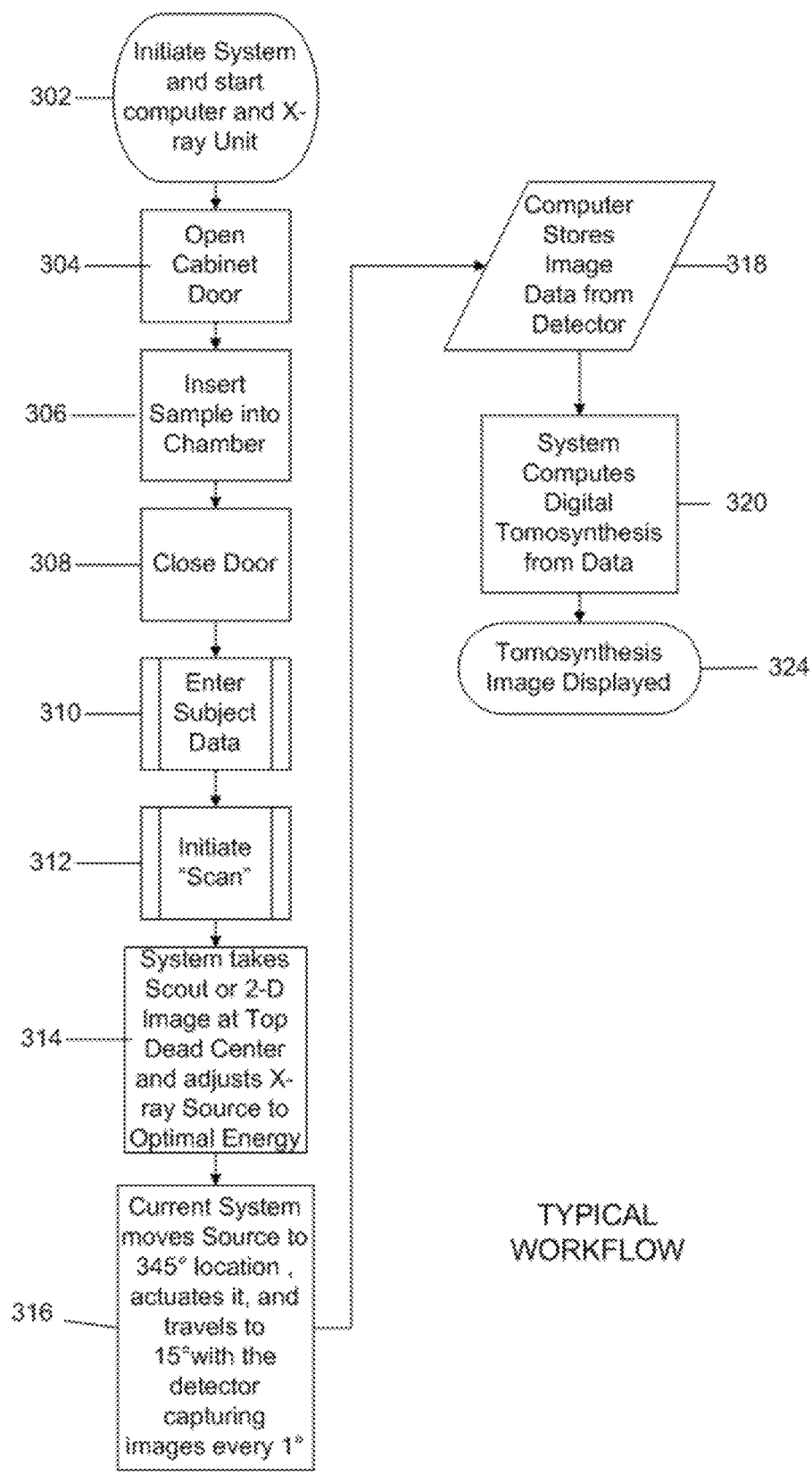
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions using, for example, the swing arm 60 (FIG. 5) with servo mechanism (the latter connected to and motion controlled by, for example, computer 470) to which the x-ray source is mounted, such as positions 12 and 16, and the detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Other embodiments of a system 100 incorporating aspects of the present disclosure are illustrated in FIGS. 1 and 2 where system 100 is totally enclosed or housed in an x-ray cabinet 22 and the x-ray source 10 is stationary relative to the stationary sample, 18 and can be used to obtain a 2-D image. In these embodiments, x-ray source 10 can be positioned at position 14 and the reference "C" refers to the point source of the x-ray beam and the reference "M" refers to the spread or fan of the x-ray beam. While the detector 20 may move or rotate, in accordance with one aspect of the present disclosure, the detector 20 can remain stationary relative to the sample 18 and x-ray source 10 to maintain an equidistant center point. The sample 18 also referred to as the "object" or "imaging object" may be disposed on or rest on the specimen platform 19 (which is a protective cover) or other surface of the detector 20. As with the previous embodiments described herein, the inventive aspects of the present disclosure differ from the prior art in that in prior art systems either the detector and x-ray source 10 and/or the isocenter is above the sample and not at the detector surface. In operation, source 10 is energized to emit an x-ray beam at position 14, located at approximately 0°, and thereby obtain a 2-D image of sample 18. In operation, source 10 is energized to emit an x-ray beam, generally throughout its travel along one or more of the paths or positions described above. The x-ray beam travels through the sample 18 to the detector 16 and a 2-D image is stored. The x-ray source 10 may range from about 0 kVp to about 90 kVp, preferably a 50 kVp 1000 μa x-ray source.

Figure 4:
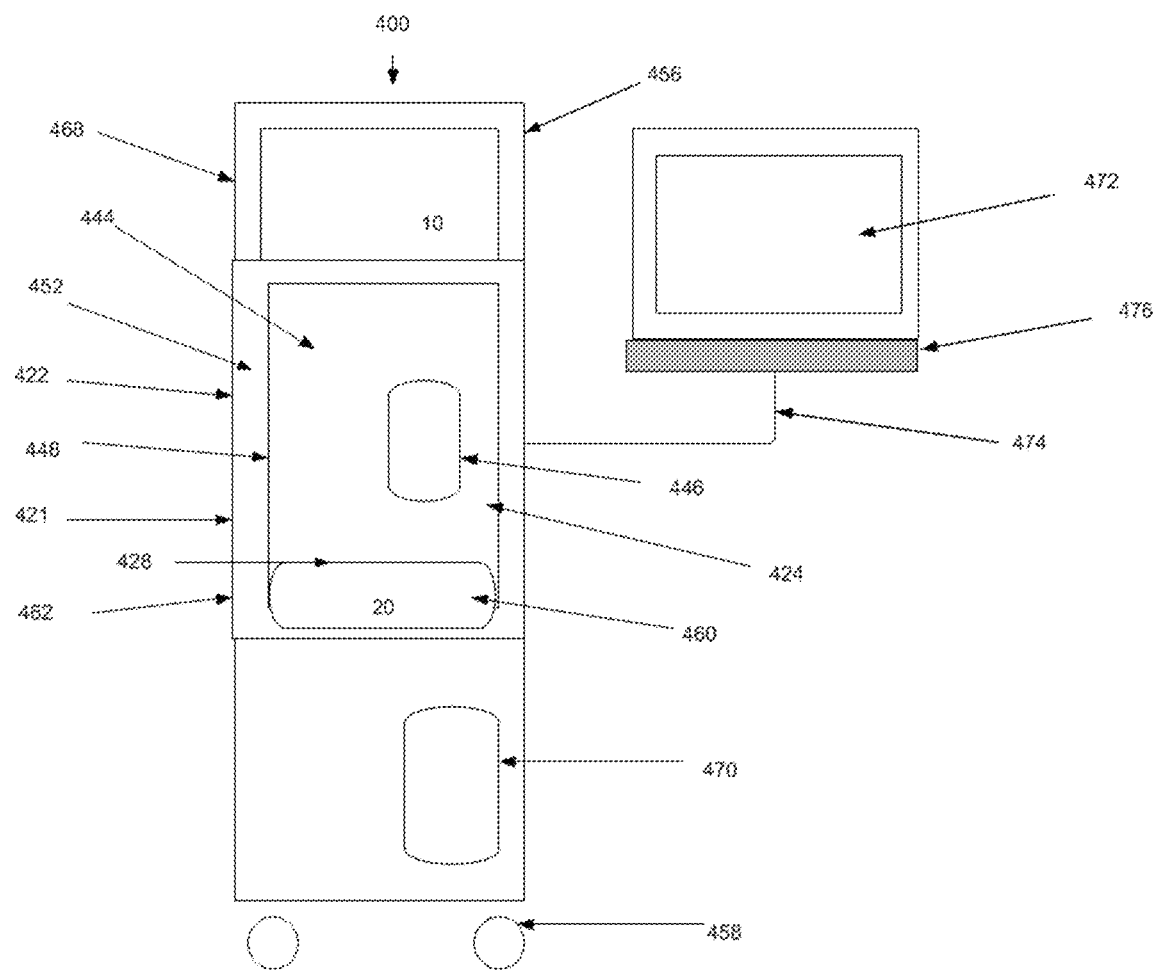
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
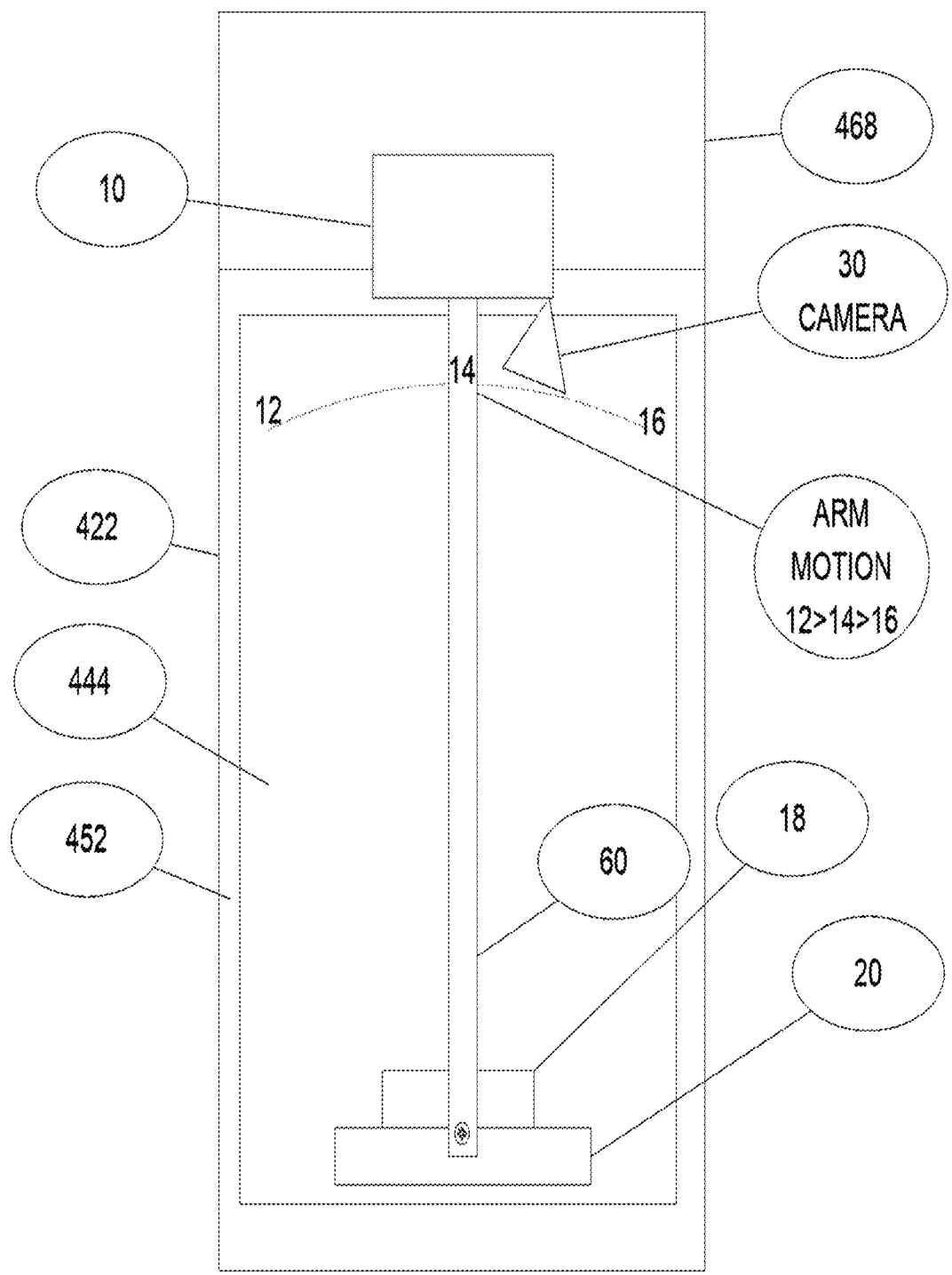
FIG. 5—Displays the sample chamber of the embodiment of FIG. 4 with the swing arm and a detector.
Figure 6:
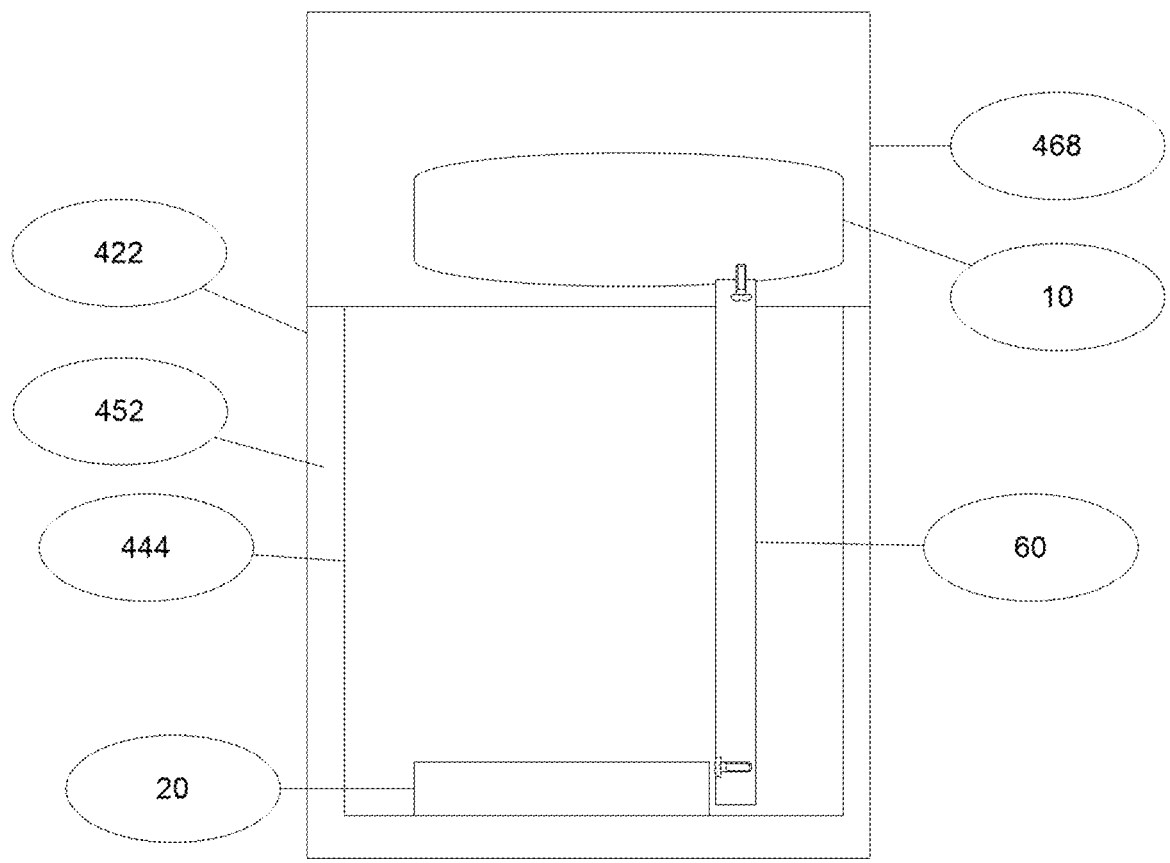
FIG. 6—Displays the lateral view of the X-ray source of the embodiment of FIG. 4 mounted to the top of the swing arm.

In one embodiment, a controller or computer 470 controls the collection of data from the detector 20, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, minicomputers, tablets and pad devices.

The computer 470 can be configured to communicate with the components of the X-ray cabinet system 400 and X-ray cabinet system 1400 in FIG. 14 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving as a result of the servo mechanism disclosed above along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images of the images of the embodiments of the present disclosure they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications.

Figure 7A:
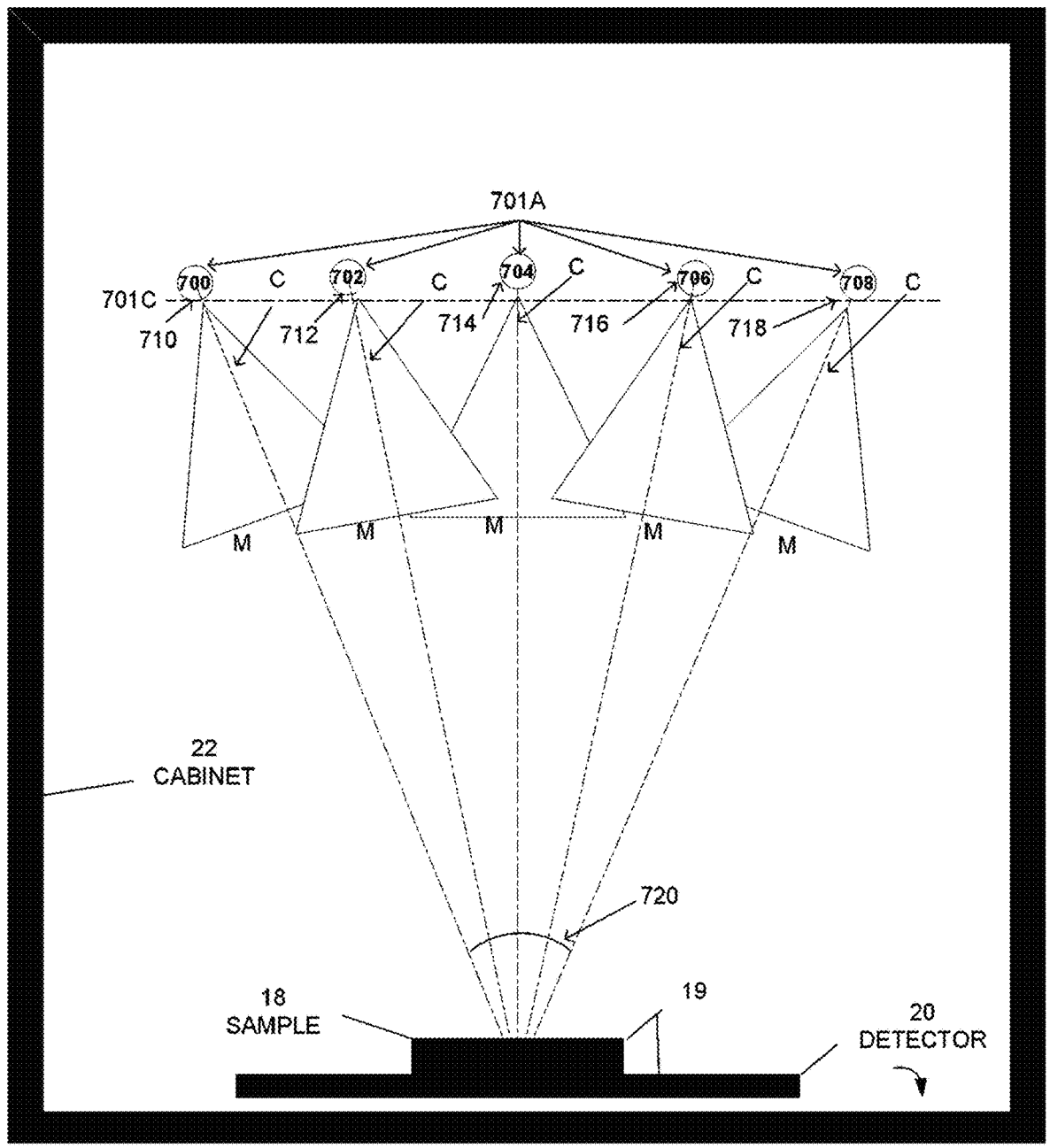
FIGS. 7A—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.
Figure 7B:
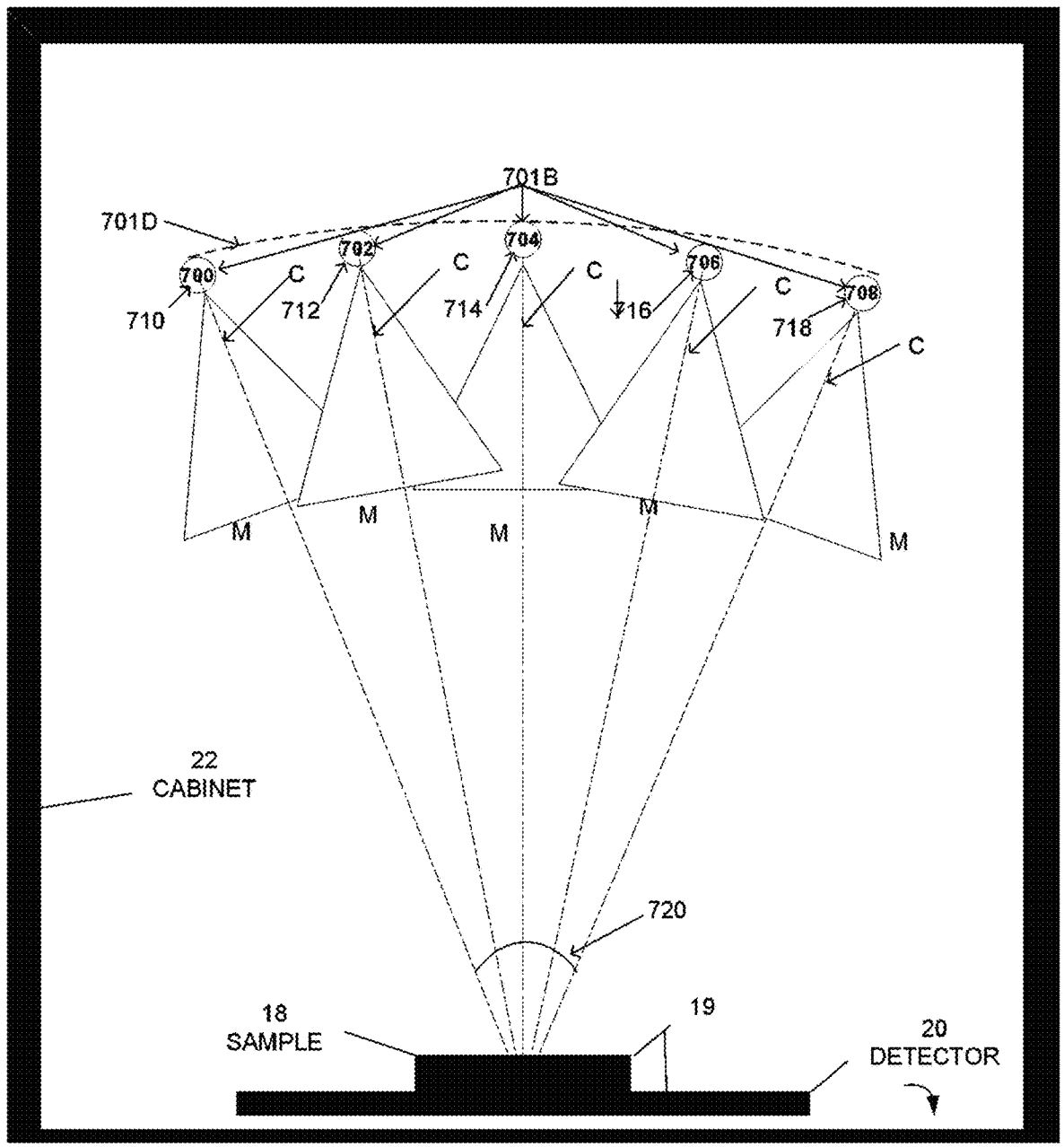
FIGS. 7B—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.

Another embodiment of the present disclosure is illustrated in FIGS. 7A and 7B that operate and include the aspects and features illustrated in the embodiments of FIGS. 1-6 except the embodiments of FIGS. 7A and 7B include an array or plurality of fixed x-ray sources at fixed points, for example, x-ray sources 700, 702, 704, 706 and 708 in place of the travel of x-ray source 10 moving (FIG. 1) swing arm 60 (FIG. 5) servo mechanism. 710, 712, 714, 716 and 718 illustrate exemplary positions of x-ray sources 700, 702, 704, 706 and 708, respectively. An optical camera and NIR system similar to those included in the present disclosure can be incorporated into the embodiments in FIGS. 7A and 7B as they are incorporated into other embodiments of the present disclosure.

The aspects of the embodiments illustrated in FIGS. 7A and 7B include at least one array or plurality of x-ray sources 701A positioned in a linear shaped arrangement along substantially linear axis 701C, as shown in FIG. 7A or at least one array or plurality of x-ray sources 701B positioned in an arc shaped arrangement along arc or curved axis 701D, as shown in FIG. 7B. The reference "C" at each of the x-ray sources 700, 702, 704, 706 and 708 in FIGS. 7A and 7B refers to the point source of the X-ray beam from each x-ray source. The reference "M" refers to the spread or fan of the X-ray beam from each x-ray source.

X-ray sources 700, 702, 704, 706 and 708 can be distributed at positions 710, 712, 714, 716 and 718, respectively, in FIGS. 7A and 7B with the end positions of the array, for example, between the point source "C" line of the beam of 700 at position 710 and the point source "C" line of the beam of 708 at position 718, are separated by an arc 720 of from about 20° to about 50°, preferable about 30°, more preferable about 20° with one x-ray source, for example, the point source "C" line of the beam of 704 at position 714 positioned at about 0°. The other x-ray sources 702 at position 712, and 706 at position 716 can be positioned such that each of those x-ray sources are positioned in between x-ray sources 700 and 708 along linear axis 701C, as shown in FIG. 7A or arc or curved axis 701D, as shown in FIG. 7B, preferably evenly spaced. The following are exemplary positions for the embodiments of FIGS. 7A and 7B can be used. Exemplary Configuration 1—about 350° (reference position 710), about 355° (reference position 712), about 0° (reference position 714), about 5° (reference position 716) and about 10° (reference position 718); Exemplary Configuration 2—about 340° (reference position 710), about 350° (reference position 712), about 0° (reference position 714), about 10° (reference position 716) and about 20° (reference position 718); Exemplary Configuration 3—about 335° (reference position 710), about 347.5° (reference position 712), about 0° (reference position 714), about 12.5° (reference position 716) and about 25° (reference position 718); between approximately 340° (reference position 12) to 0° (reference position 14) to 20° (reference position 16) and or between approximately 335° (reference position 12) to 0° (reference position 14) to 25° (reference position 16).

In another embodiment, X-ray sources 700, 702, 704, 706 and 708 can be positioned at 710, 712, 714, 716 and 718, respectively, in FIGS. 7A and 7B, such that the point source "C" line of the beam of each the x-ray sources at either end of the array, the point source "C" line of the beam of 700 at position 710 and the point source "C" line of the beam of 708 at position 718, are separated by an arc 720 of from about 20° to about 50° arc, preferable about 30°, more preferable about 20°, with one x-ray source the point source "C" line of the beam of 704 at position 714 is positioned at about 0°. The other x-ray sources 702 at position 712, and 706 at position 716 can be positioned such that the point source "C" of the beam of each of those x-ray sources are positioned within arc 720, preferable with the point source "C" line of the beams of x-ray sources 702 at position 712, 704 at position 714 and 706 at position 716 are evenly distributed between the point source "C" line of the beam x-ray sources 700 at position 710 and 708 at position 718. For example, x-ray source 700 can be positioned with a point source "C" line of the beam thereof at about 350°, x-ray source 702 can be positioned with a point source "C" line of the beam thereof at about 355°, x-ray source 704 can be positioned with a point source "C" line of the beam thereof at about 0°, x-ray source 706 can be positioned with a point source "C" line of the beam thereof at about 5° and x-ray source 708 can be positioned with a point source "C" line of the beam thereof at about 10°. For another example, x-ray source 700 can be positioned with a point source "C" line of the beam thereof at about 340°, x-ray source 702 can be positioned with a point source "C" line of the beam thereof at about 350°, x-ray source 704 can be positioned with a point source "C" line of the beam thereof at about 0°, x-ray source 706 can be positioned with a point source "C" line of the beam thereof at about 10° and x-ray source 708 can be positioned with a point source "C" line of the beam thereof at about 20°. For still another example, x-ray source 700 can be positioned with a point source "C" line of the beam thereof at about 335°, x-ray source 702 can be positioned with a point source "C" line of the beam thereof at about 347.5°, x-ray source 704 can be positioned with a point source "C" line of the beam thereof at about 0°, x-ray source 706 can be positioned with a point source "C" line of the beam thereof at about 12.5° and x-ray source 708 can be positioned with a point source "C" line of the beam thereof at about 25°.

The ranges recited herein are intended to be approximate and inclusive of start and endpoints.

The number of x-ray sources in the arrays or pluralities of x-ray sources 701A and 701B can range from a minimum total of at least about 3 to about 11 or more, about 5 to about 11 (preferably about 5, about 7, about 9, about 11) including preferably an odd number of x-ray sources, further including for each of these aforementioned ranges wherein one of the x-ray sources is positioned at about 0° or the point source "C" line of one of the x-ray beams is positioned at about 0°. An alternative embodiment can include arrays or pluralities of x-ray sources 701A and 701B distributed such that the point sources of adjacent x-ray sources in the array or plurality are separated by about 1° to about 5°, preferably about 1°. As with other embodiments of the present disclosure the x-ray detector 20 is stationary as is the sample 18 and the x-ray detector can include, for example, a flat panel x-ray detector including a flat panel digital x-ray detector.

The x-ray cabinet 22, the detector 20, the sample 18 and the specimen platform 19 (which is a protective cover) or other surface of the detector 20 are the same as included in the embodiment of FIG. 1. As with other embodiments of the present disclosure, the isocenter of the image acquisition geometry is located below the sample, on the surface of the detector.

Each x-ray source of the array or plurality (e.g., x-ray sources 700, 702, 704, 706 and 708) can be activated to emit an x-ray beam one at a time so that the detector 20 receives only one image at a time. The sequence of activating the x-ray sources can be random, but preferably, from left to right (e.g., first 700, second 702, third 704, fourth 706 and fifth 708) or right to left (e.g., first 708, second 706, third 704, fourth 702 and fifth 700).

Operation of the embodiments of FIGS. 7A and 7B that is different from what is included in the present disclosure in FIG. 3 includes at 316 the detector 20 capturing images from x-rays emitted from each of the fixed x-ray sources ((e.g., x-ray sources 700, 702, 704, 706 and 708) that are included in the array or plurality of x-ray sources and storing the captured image along with the identification of the specific x-ray source ((e.g., x-ray sources 700, 702, 704, 706 and 708) from which it originated, using the latter information to identify the position of the x-ray source relative to the sample. The captured images and identification of the specific x-ray source ((e.g., x-ray sources 700, 702, 704, 706 and 708) from which each originated are stored 318 and digital tomosynthesis is performed 320. The tomosynthesis image is then displayed 324.

One advantage of having a fixed array of x-ray sources (compared to, for example, having one x-ray source that is moved by, e.g., a motion control mechanism) is the elimination of moving parts needed to move the single x-ray source, the elimination of vibration caused by x-ray source movement during use which could cause blurring or artifacts, the faster acquisition of x-ray images as energizing each of the plurality of x-ray sources need only rely on computer controlled (e.g., computer 470) and don't need to wait until the single x-ray source is moved into position, and a more precise angle resolution because each of the x-ray source in the plurality or array are fixed in position rather than having to rely on a moving x-ray source where its position can be less precise during operation.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in plane resolution and image quality during magnification for greater diagnostic confidence. Software is optimized for performance using GPU Technology.

The reconstruction software used in conjunction with the aspects of the present disclosure provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the detector 20. The aspects of the present disclosure provide for the reconstruction plane to be angled with respect to the detector plane.

Figure 8:
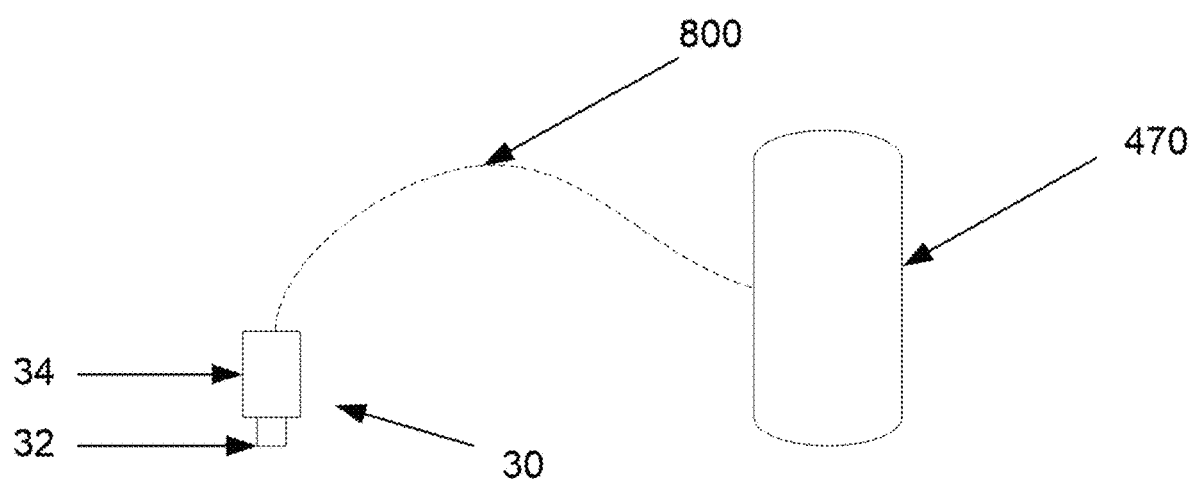
FIG. 8—Displays an interconnection diagram of an HD camera embodiment that may be utilized in aspects of the disclosed embodiments of the present disclosure.

FIGS. 8, 9, 10A and 10B depict various features of embodiments of the present disclosure, which embodiments are generally directed to a system that can utilize an optical camera, preferably a real-time camera, to capture a visual image of a specimen/sample concurrently or at substantially the same time as the acquisition of an x-ray image. Referring to FIG. 8, there is shown the interconnection of an embodiment of a camera 30 incorporated into a Cabinet X-Ray Unit which connects to and can be controlled by the computer 470 via cable 800 including, for example a USB cable. Other wireless formats for communication between camera 30 and computer 470 can also be used in embodiment of the present disclosure. Camera 30 may include an optical lens assembly 32 through which an optical image passes and is focused upon an electronic light-sensitive sensory array included in the camera body 34. The optical image can then be sent using an electronic signal from the sensory array to the computer 470 via cable 800 or other wireless formats. The optical image as well as a 2-D x-ray image or tomosynthesis image can also be stored in the computer 470 for future examination and viewing, including storage in memory (e.g., RAM) or a disc recording medium (e.g., CD, DVD, etc.)

Camera 30 is included in FIGS. 1, 2 and 5 as well showing embodiments in camera 30, for example, located at position 15 in the cabinet x-ray unit such that it is capable of capturing a visual image of sample 18 in cabinet 22 and x-ray cabinet chamber 28 in FIGS. 1 and 2 and in cabinet 422 and sample chamber 444 in FIG. 5, preferably such that the optical image captured by camera and the x-ray image (2-D x-ray image or tomosynthetic x-ray image) show the sample or specimen at substantially, preferably exactly, the same orientation for the optical and x-ray images. In one embodiment, a medical professional or other authorized operator places a specimen/sample into the chamber, closes and secures the door, and presses, for example, the "acquire" command on the system using, for example, a keyboard or touch screen monitor that can be used to enter system commands or other information. In one embodiment, pressing this command can simultaneously or in substantially close proximity in time, the computer commands the optical camera, NIR system and x-ray source in conjunction with the x-ray detector to capture images from the three components, the latter being an x-ray image or series of images from which tomosynthetic images can be assemble. In another embodiment, as a result of pressing this command, the x-ray source in conjunction with the x-ray detector captures an x-ray image or series of images from which tomosynthetic images can be assemble. The resulting x-ray image or tomosynthetic image can them be displayed at the same time as or separately from a real-time optical image is captured through the camera with at least one of these images included along with an NIR image.

In the systems and methods included in this disclosure as well as the embodiments disclosed herein, the resulting NIR system, x-ray generated and optical camera images can be displayed each alone or together as overlaid together, adjacent or PIP (Picture-in-Picture) on the monitor FIGS. 4 and 14-472. This, in turn, provides more flexibility for a clinician or other user of the system and simplifies the procedure. The separate images from the camera, NIR system and x-ray detector separately as well as the tomosynthetic, overlaid, adjacent and PIP images can be stored in the computer hard drive on the system 470 or a separate memory device, such as for example, a separate hard drive, flash drive, CD-ROM, DVD, etc. for future analysis. The camera can capture a visible light or other electromagnetic wavelength reflected or emitted by the sample or portions thereof, for example, though the use of fluorescent or other markers using a suitable light source where required. Manual input for operation of the cabinet x-ray unit may be initiated via keyboard or monitor touch screen and the resulting image from both the manual-initiated examination can be displayed on the screen and configured in accordance with one example embodiment of the present disclosure.

Figure 9:
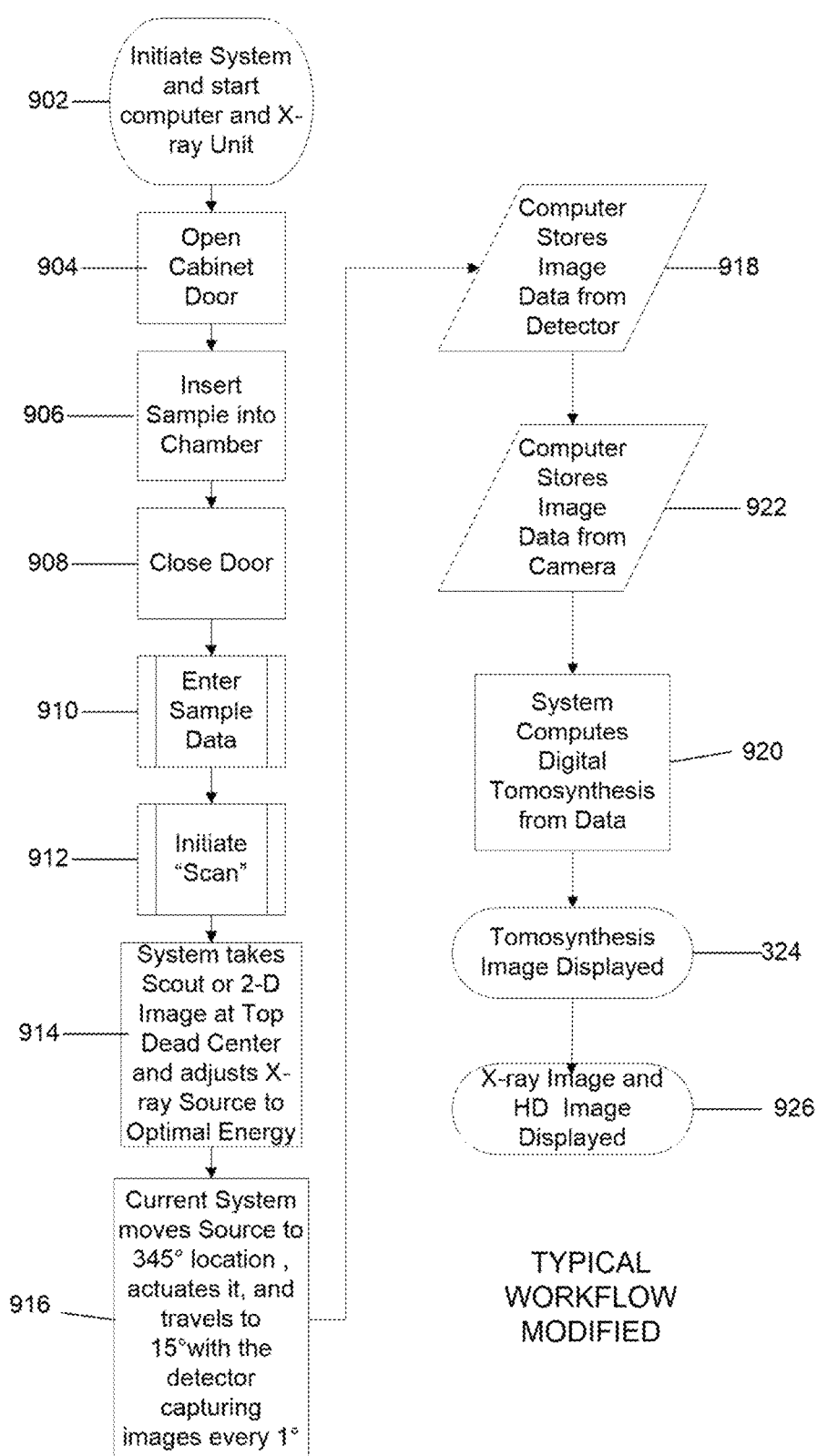
FIG. 9—Displays an exemplary modified workflow/flowchart of an aspect of the disclosed embodiments.

FIG. 9 illustrates one embodiment of a modified basic workflow of the cabinet x-ray unit with the addition of the storage of the image data 922 and the combination x-ray image and HD image displayed 926.

As will be generally understood, the system 100 is initiated 902, the X-ray cabinet door 24 opened 904, and the sample 18 placed into 906 the X-ray cabinet chamber 28. As shown in FIG. 2, for example, the sample 18 is positioned on the detector 20 in a suitable manner. The door 24 is closed 908.

Figure 11:
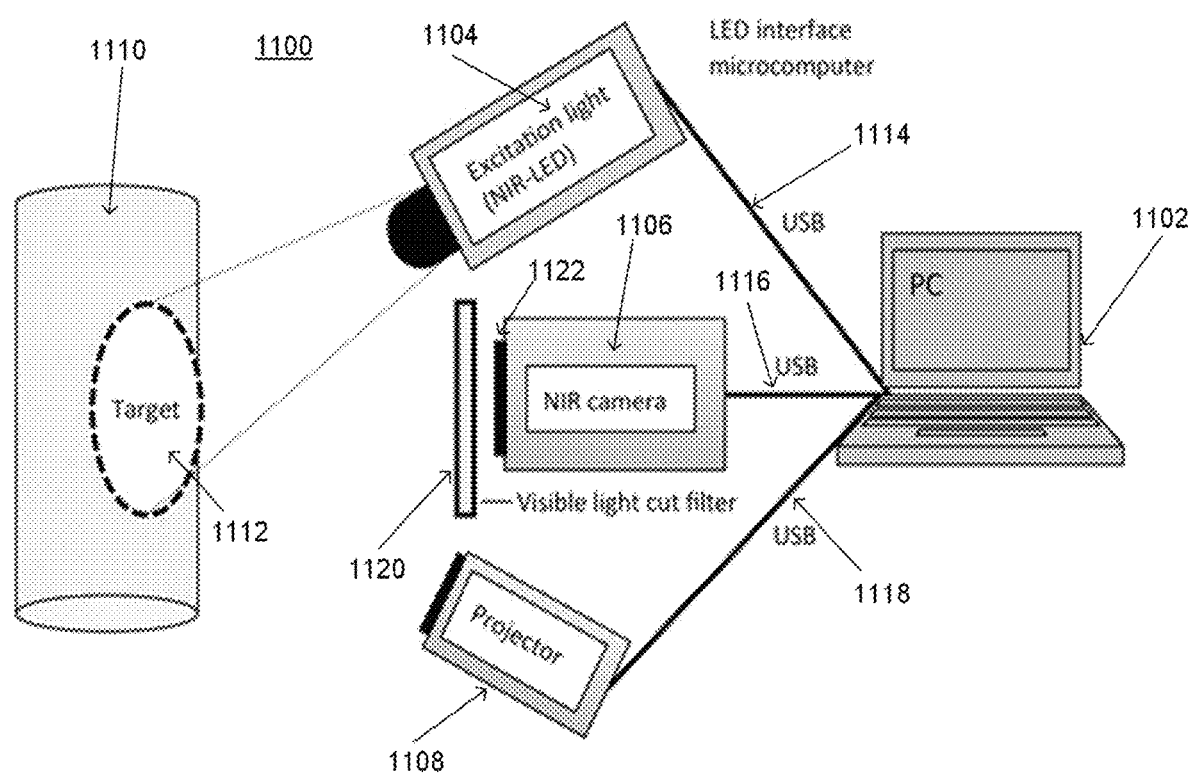
FIG. 11—Displays an interconnection diagram of a NIR Projector and camera embodiment that may be utilized in aspects of the disclosed embodiments of the present disclosure.

The data and information regarding the sample 18, including any other suitable information or settings relevant to the imaging process and procedure, is entered 910 into the computer 470. The scan is initiated 912. The system 100 will take 914 scout or 2-D images at Top Dead Center, which for purposes of this example is position 14 of FIGS. 1 and 2. The X-ray source 10 can then be moved to other positions, such as positions 12 and 16, and the detector 20 can be used to capture 916 images at various increments along the travel path of the X-ray source 10, such as about every 1 degree. An optical image, for example, an HD image, is captured by the camera and stored in the computer 922. The captured images are stored 918 and digital tomosynthesis is performed 920. The tomosynthesis image is then displayed 924. The combination x-ray image and HD image are then displayed 926, the x-ray image can be either the 2-D image from 914 or the tomosynthesis image from 920. Another embodiment of the workflow embodiment illustrated in FIG. 9 can include obtaining a 2-D x-ray image as in 914 without the detector 20 being used to capture 916 images at various increments along the travel path and related steps 920 and 924 related to tomosynthesis FIG. 10A exhibits the HD image of a breast specimen and FIG. 10B exhibits the x-ray image of the specimen showing the actual placement of the markers 1002 and orientation of the specimen as well as placement of the markers 1002 within the breast specimen 1000. Markers 1002 are utilized to delineate the outer boundaries of the suspect area that needs to be excised in the X, Y, and Z directions. The markers may include radioactive seeds, coils, wires, and/or radiopaque/visible items which are implanted before the surgery by an interventional radiologist prior to the surgery and are utilized to denote boundaries of the region of interest. i.e. areas of cancer or densities FIG. 11 schematically illustrates one embodiment of an NIR system and the components thereof that may be utilized in aspects of the disclosed embodiments of the present disclosure. This system can be positioned within the cabinet or on the exterior thereof as disclosed herein. The system 1100 includes a computer 1102 such as a microcomputer or computer 470 included in embodiments of the present disclosure. Computer 1102 controls and is connected to the NIR excitation light 1104 (such as for example, an NIR light emitting diode (NIR-LED) and the NIR camera/detector 1106 and may also include a projector 1108). Connections between the computer 1102 and the NIR excitation light 1104, the NIR camera 1106 and projector 1108 via connection conduits 1114, 1116 and 1118, respectively, can be a wired or wireless connection conduits as included in the present disclosure or understood in the art. If 1114, 1116 and 1118 are wired conduits, they may provide power from computer 1102 to the components to which they are connected. If 1114, 1116 and 1118 are wireless, components 1104, 1106 and 1108 are powered via a self-contained device (e.g., a battery or other power storage device) or are each connected to a separate power source (e.g., an electrical source such as an electrical wall socket or separate power source (e.g., a battery or other power storage device)). The NIR excitation light 1104 is aimed at the target 1110 (e.g., sample or specimen) and is activated by the computer 1102 to project NIR light toward the target area 1112 of the target to excite those portions within the target area 1112 capable of emitting NIR fluorescence, for example, areas including indocyanine green (ICG). The NIR camera 1106 is controlled by the computer 1102 to record an image of the target area 1112 emitting NIR fluorescence through lens 1122 focused on target area 1112 which the computer 1102 stores. The system may also include a visible light cut filter 1120. The projector 1108 is also connected to and controlled by computer 1102 and can be used, for example, with the other embodiments of the present disclosure that include an optical camera in order to provide lighting directed toward the target 1110 thereby resulting in a better visual image (i.e., a better lit target 1110).

Figure 12:
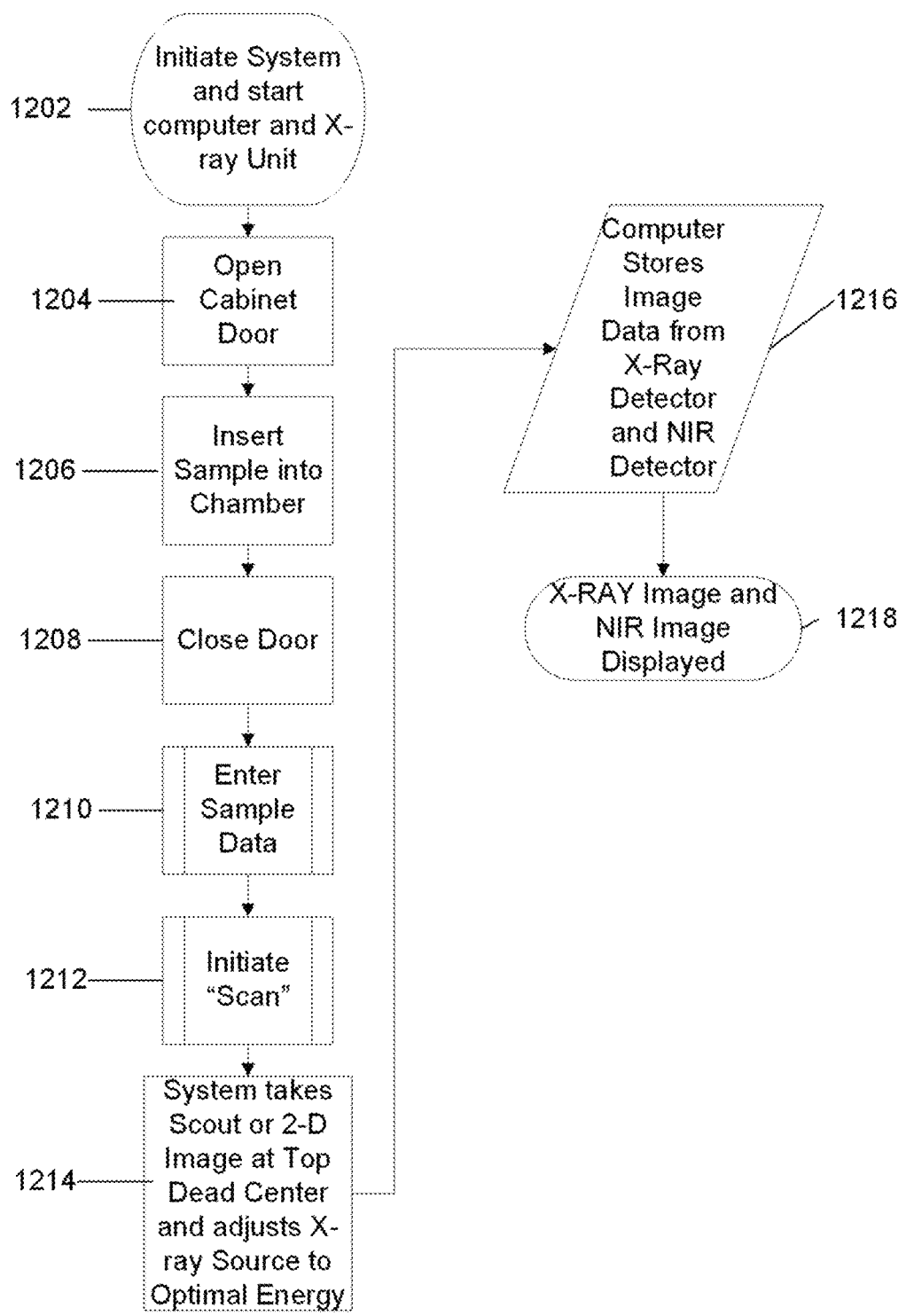
FIG. 12—Displays an exemplary workflow/flowchart of a system incorporating an aspect of the disclosed embodiments.

FIG. 12 illustrates one embodiment of a modified basic workflow of the cabinet x-ray unit embodiments of the present disclosure including an NIR system that can be located within or external to the cabinet x-ray unit embodiment.

As will be generally understood, one of the system embodiments of the present disclosure is initiated 1202, the X-ray cabinet door 24, for example, opened 1204, and the sample 18, for example, placed into 1206 the X-ray cabinet chamber 28, for example. As shown in FIG. 2, for example, the sample 18 is positioned on the detector 20 in a suitable manner. The door 24 is closed 1208.

The data and information regarding the sample 18, for example, including any other suitable information or settings relevant to the imaging process and procedure, is entered 1210 into the computer 470, for example. The scan is initiated 1212. The system 100, for example, will take 1214 scout or 2-D images at Top Dead Center, which for purposes of this example is position 14 of FIGS. 1 and 2, for example, and store those images at 1216. Also in 1212, the X-ray source 10, for example, can then be moved to other positions, such as positions 12 and 16, and the detector 20 can be used to capture and stored 1216 images at various increments along the travel path of the X-ray source 10, such as about every 1 degree, for example. An optical image, for example, an HD image, is captured by the camera 1214 and stored in the computer 1216. Further in 1212, an NIR image can also be taken and stored in 1216 in which the specimen is inside the cabinet and taken by an NIR system inside the cabinet or the specimen is removed from the cabinet and the NIR image is taken by an NIR system outside the cabinet and stored in 1216 The captured images are stored 1216 and digital tomosynthesis can be performed. The tomosynthesis image and/or the 2-D x-ray image can then be displayed with the NIR image 1218. Another embodiment of the workflow embodiment illustrated in FIG. 12 can include obtaining a 2-D x-ray image as in 1214 without the detector 20 being used to capture and store 1216 images at various increments along the travel path. AN optical image can also be optionally displayed at 1218.

One embodiment of the present disclosure is illustrated in FIG. 13 that includes the embodiment of FIG. 1 of the present disclosure, but also includes additional aspects. The system 1300 is totally enclosed or housed in an X-ray cabinet 22 and also includes an NIR system and illustrates an embodiment in which an NIR system is positioned within an x-ray cabinet along with the other aspects included in both FIGS. 1 and 13. The NIR system is positioned inside X-ray cabinet 22 of the present disclosure and includes an NIR excitation light 40 and a dual purpose optical camera and NIR camera/detector 42. Although the dual purpose optical camera and NIR camera/detector 42 are shown as a single unit, they can be included in embodiments of the present disclosure where they are separate such that optical camera 30 is separate from NIR camera/detector 44.

The NIR system includes the NIR excitation light 40 and the dual purpose optical camera and NIR camera/detector 42 of FIG. 13 is positioned in the cabinet x-ray unit such that the NIR excitation light 42 is capable of projecting NIR light toward x-ray detector 20 and sample 18 positioned thereon and the dual purpose optical camera and NIR camera/detector 42 is capable of receiving and recording an NIR image of sample 18 emitting NIR fluorescence, preferably such that the NIR image captured by the dual purpose optical camera and NIR camera/detector 42 and the other images (the optical image and the x-ray image (2-D x-ray image or tomosynthetic x-ray image)) show the sample 18 at substantially, preferably exactly, the same orientation where such selection of images at the same orientation may be performed by a computer, for example, computer 470. In one embodiment, a medical professional or other authorized operator places a specimen/sample into the chamber, closes and secures the door, and presses, for example, the "acquire" command on the system using, for example, a keyboard or touch screen monitor that can be used to enter system commands or other information. In one embodiment, pressing this command can simultaneously or in substantially close proximity in time, the computer commands the NIR system, and one or both of the optical camera and x-ray source in conjunction with the x-ray detector to capture images from the those sources, the latter being an x-ray image or series of images from which tomosynthetic images can be assemble. In another embodiment, as a result of pressing this command, the x-ray source in conjunction with the x-ray detector captures an x-ray image or series of images from which tomosynthetic images can be assembled. The resulting x-ray image or tomosynthetic image can then be displayed at the same time as the NIR image and a real-time optical image is captured through the camera.

In the systems and methods included in this disclosure as well as the embodiments disclosed herein, the resulting x-ray generated, NIR and optical camera images can be displayed each alone or any two or all three together as overlaid together with or without any of the images adjacent or PIP (Picture-in-Picture) on the monitor FIG. 4—472 as controlled by the computer 470. This, in turn, provides more flexibility for a clinician or other user of the system and simplifies the procedure. The separate images from the optical camera, the NIR camera/detector and x-ray detector separately as well as the tomosynthetic, overlaid, adjacent and PIP images can be stored in the computer hard drive on the system 470 or a separate memory device, such as for example, a separate hard drive, flash drive, CD-ROM, DVD, etc. for future analysis. The optical camera can capture a visible light or other electromagnetic wavelength reflected or emitted by the sample or portions thereof, for example, though the use of fluorescent or other markers using a suitable light source where required. Manual input for operation of the cabinet x-ray unit may be initiated via keyboard or monitor touch screen and the resulting image from both the manual-initiated examination can be displayed on the screen and configured in accordance with one example embodiment of the present disclosure.

Another embodiment of the present disclosure is illustrated in FIG. 14 that includes the embodiment of FIG. 4 of the present disclosure, but also includes additional aspects. The system 1400 includes an NIR system and illustrates an embodiment in which an NIR system is mounted or positioned on the exterior of an x-ray cabinet along with the other aspects included in both FIGS. 4 and 14. The NIR system can be mounted or positioned on any surface (e.g., vertical or horizontal surface) of any part of the exterior of X-ray Cabinet System 1400 of the present disclosure, for example, on the upper part 456 of the cabinet 422. The NIR system includes an NIR excitation light and camera/detector 1490 as a single unit, such as, for example, Thermo Scientific Antaris II FT-NIR Analyzer, that is mounted to an arm assembly 1480. The NIR excitation light and camera/detector 1490 can be moveably (e.g., rotatably) mounted to arm assembly 1480 (for example a "C" arm) at one end of the arm and the latter can be moveably (e.g., rotatably) mounted at the other end of the arm to the upper part 456 of the cabinet 422 or whatever surface (e.g., vertical or horizontal surface) of any part of the exterior of X-ray Cabinet System 1400. In another embodiment, arm assembly 1480 can also include the apparatus included in U.S. Pat. No. 10,492,747, entitled "SYSTEM AND METHOD FOR EXTENDING AND RETRACTING A MOVEABLE ARM," the disclosure of which are hereby incorporated by reference in its entirety. As a result of being moveable, the sample or specimen (preferably in a tray or other surface on which it can rest) can be positioned on a substantially flat surface (either part of system 1400 or separate therefrom) within an acceptable distance of the NIR excitation light and camera/detector 1490 so that an acceptable image of the sample or specimen can be obtained. For example, the NIR excitation light and camera/detector 1490 and arm assembly 1480 can be moved so that the sample or specimen can be placed on surface 1485 the upper part 456 of the cabinet 422. In one embodiment, a controller or computer 470 controls the collection of data from the NIR system of embodiments of the present disclosure as well as other features and uses included in the present disclosure. In FIG. 14, the present disclosure also includes embodiments where NIR excitation light 40 and NIR camera/detector 40 are included in a single unit, such as, for example, Thermo Scientific Antaris II FT-NIR Analyzer. The computer 470 can be configured to communicate with the components of the system 1400 or system 1300 in any suitable manner, including hard wired and wireless communication using various known formats. In one embodiment, the computer 470 can be configured to communicate over a network, such as a Local Area Network or the Internet.

Figure 15A:
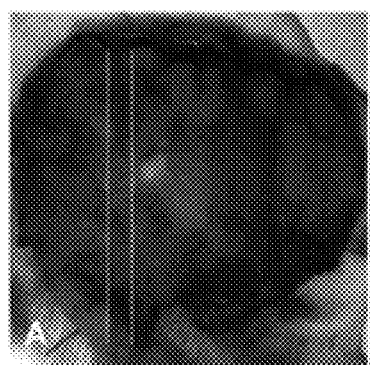
FIGS. 15A to 15L—are greyscale images displaying HD, NIR and overlay images of a breast specimen made using exemplified embodiments of the present disclosure.
Figure 15B:
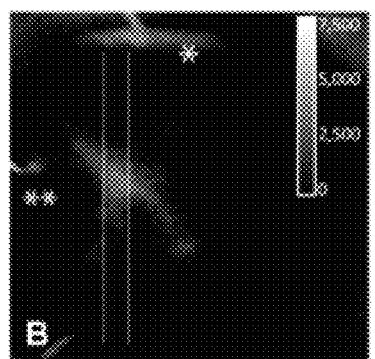
Figure 15C:
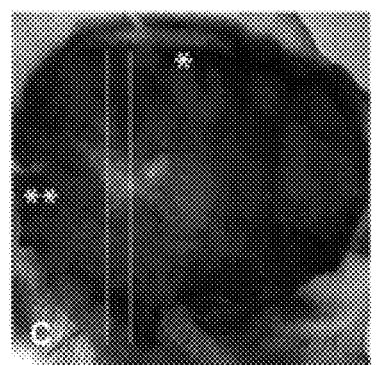
Figure 15D:
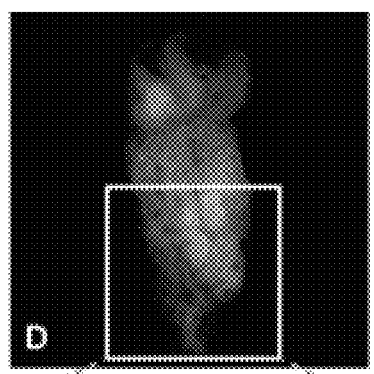
Figure 15E:
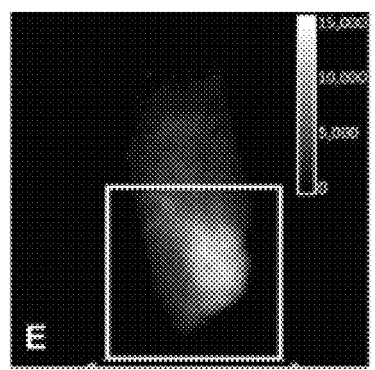
Figure 15F:
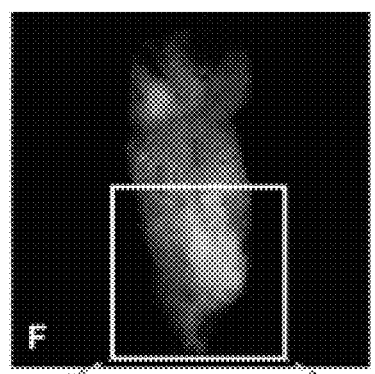

Specimens from one patient were identified with a microscopic irradical resection (i.e., the positive margin) upon histopathologic analysis of the excised tissue lump shown in FIGS. 15A-15L. In some of the images, a fluorescent signal (indocyanine green (ICG) indicating a tumor was detectable at the positive resection margin of the excised lump. FIG. 15A is a grayscale image, of the excised lump ex-vivo utilizing white light. FIG. 15B is a grayscale image of the excised lump ex-vivo utilizing fluorescence. FIG. 15C is a grayscale image of the excised lump ex-vivo of an overlay of the images of FIGS. 15A and 15B with pseudocolor. Although the tumor is not visible during surgery, it clearly visible on the back table during the surgical procedure and after bread-loaf slicing. FIG. 15D is a grayscale image of the excised lump after bread loaf slicing utilizing white light. FIG. 15E is a grayscale image of the excised lump after bread loaf slicing utilizing fluorescence. FIG. 15F is a grayscale image of the excised lump after bread loaf slicing of an overlay of the images of FIGS. 15D and 15E with pseudocolor.

Figure 15G:
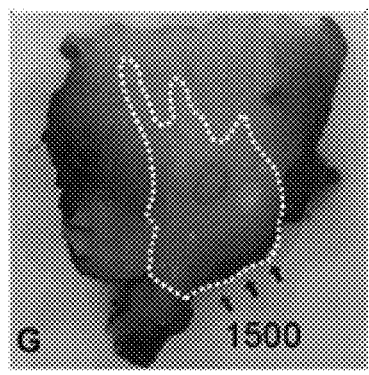
Figure 15H:
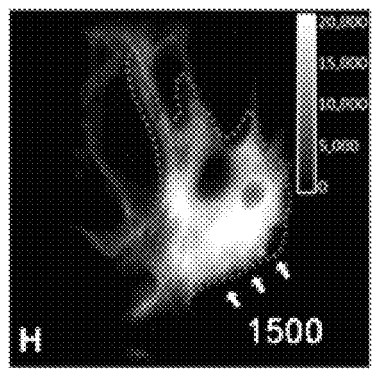
Figure 15I:
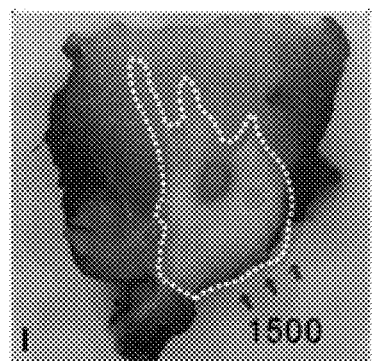

Paraffin embedding is a known technique used in clinical and research environments to create a formalin-fixed, paraffin-embedded (FFPE) block of tissue in which formalin-fixed tissue undergoes tissue processing and then is embedded in paraffin (wax) to create a FFPE block or paraffin block. FFPE is used to preserve and prepare biopsy specimens for examination, experimental research, and diagnostic/drug development. The paraffin block (FIGS. 15G-15I) also showed a clear positive signal at the tumor site. FIG. 15G is a grayscale image of a paraffin block of the excised lump utilizing white light. FIG. 15H is a grayscale image of a paraffin block of the excised lump utilizing fluorescence. FIG. 15I is a grayscale image of a paraffin block of the excised lump of an overlay of the images of FIGS. 15G and 15H with pseudocolor.

Figure 15J:
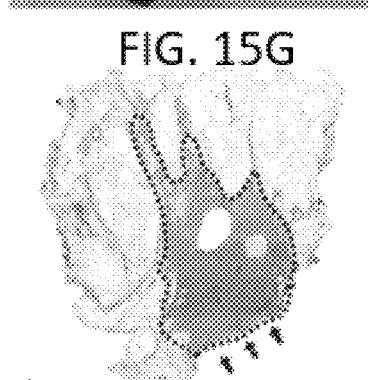
Figure 15K:
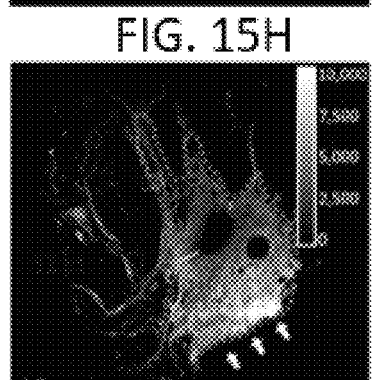
Figure 15L:
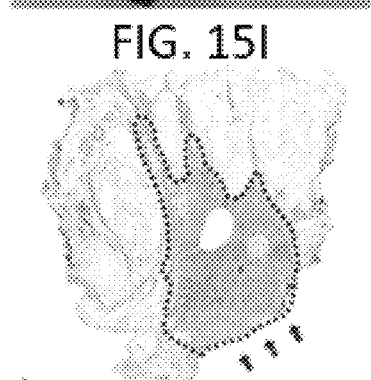

Haematoxylin and eosinstain (H&E) tissue staining, (FIGS. 15J-15L) which is utilized for histological findings were corroborated by fluorescence flatbed scanning of the indocyanine green (ICG) images (FIG. 15K) and an overlay image (FIG. 15L). This confirmed the presence of the NIR dye (indocyanine green (ICG)) in the tumor area and the designated positive margin of the excised tumor margin (indicated by black and white arrows 1500 in FIGS. 15G-15L). FIG. 15J is a grayscale image of the excised lump stained with haematoxylin and eosinstain (H&E) and indocyanine green (ICG) utilizing white light. FIG. 15K is a grayscale image of the excised lump stained with haematoxylin and eosinstain (H&E) and indocyanine green (ICG) utilizing fluorescence. FIG. 15L is a grayscale image of the excised lump stained with haematoxylin and eosinstain (H&E) and indocyanine green (ICG) of an overlay of the images of FIGS. 15J and 15K with pseudocolor.

Indeed, it is appreciated that the system and its individual components can include additional features and components, though not disclosed herein, while still preserving the principles of the present disclosure. Note also that the base computer can be one of any number devices, including a desktop or laptop computer, etc.

Aspects of the present disclosure may be embodied in other specific forms without departing from its spirit or essential characteristics. The described embodiments are to be considered in all respects only as illustrative, not restrictive. All changes that come within the meaning and range of equivalency of the claims are to be embraced within their scope.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

What is claimed is:

1. A cabinet x-ray and near-infrared (NIR) image system for obtaining x-ray images and NIR images of a specimen, the system comprising:
    a cabinet defining an interior chamber;
    a display;
    an x-ray system including:
        an x-ray source;
        an x-ray detector; and
        a specimen platform having a protective cover of and in physical contact with the x-ray detector;
    a motion control mechanism configured for moving the x-ray source to or along a plurality of positions within the interior chamber relative to the specimen disposed on the specimen platform;
    an NIR image system configured to capture an NIR image of the specimen, the NIR image system including:
        an NIR camera/detector; and
        an NIR excitation light; and
    a controller configured to:
        selectively energize the x-ray source to emit x-rays through the specimen to the x-ray detector at selected positions of the x-ray source relative to the specimen such that the isocenter of the emitted x-rays at the selected positions is located at a surface of the x-ray detector;
        control the x-ray detector to collect a projection x-ray image of the specimen when the x-ray source is energized at the selected positions, wherein one of the projection x-ray images is a two-dimensional x-ray image taken at standard imaging angle of approximately 0°;
        create a tomosynthetic x-ray image reconstructed from a collection of projection x-ray images;
        process the collection of the projection x-ray images in the controller into one or more reconstructed tomosynthetic x-ray images representing a volume of the specimen and relating to one or more image planes that are selectively the same or different from that of the two-dimensional x-ray image;
        control the NIR image system to capture and collect the NIR image of the specimen; and
        selectively display the NIR image and at least one of the two-dimensional x-ray image and the one or more reconstructed tomosynthetic x-ray images on the display.

2. The cabinet x-ray and NIR system of claim 1, wherein the specimen platform is configured for excised tissue, organ or bone specimens.

3. The cabinet x-ray and NIR system of claim 1, wherein the specimen platform is configured for any organic or inorganic specimen that fits inside an x-ray cabinet.

4. The cabinet x-ray and NIR system of claim 1, wherein the controller is configured to control the x-ray detector to collect a projection x-ray image of the specimen when the x-ray source is energized and control the NIR system to capture and collect the NIR image of the specimen such that the projection x-ray image and NIR image are collected at substantially the same time.

5. The cabinet x-ray and NIR system of claim 1, wherein the orientation of the specimen in the x-ray image and the NIR image are substantially the same.

6. The cabinet x-ray and NIR system of claim 1, wherein the controller is configured to selectively display the x-ray image and the NIR image on the display simultaneously side-by-side or picture-in-a-picture.

7. The cabinet x-ray and NIR system of claim 1, wherein the controller is configured to selectively display the x-ray image and the NIR image on the display overlaid.

8. The cabinet x-ray and NIR system of claim 1, wherein the NIR image system is within the walled enclosure.

9. A cabinet x-ray and near-infrared (NIR) system for obtaining x-ray images and NIR images of a specimen, the system comprising:
  a cabinet including a walled enclosure surrounding an interior chamber, a door configured to cover the interior chamber and a sampling chamber within the interior chamber for containing the specimen;
  a display;
  an x-ray system including:
    an x-ray source;
    an x-ray detector; and
    a specimen platform:
  an NIR image system configured to capture an NIR image of the specimen, wherein the NIR image system is external to the walled enclosure, the NIR image system including:
    an NIR camera/detector; and
    an NIR excitation light; and
  a controller configured to:
    selectively energize the x-ray source to emit x-rays through the specimen to the x-ray detector;
    control the x-ray detector to collect a projection x-ray image of the specimen when the x-ray source is energized;
    selectively display the x-ray image on the display;
    control the NIR image system to capture and collect the NIR image of the specimen; and
    selectively display the NIR image on the display.

10. A cabinet x-ray, near-infrared (NIR) and optical camera system for obtaining x-ray images, projection x-ray images, reconstructed tomosynthetic x-ray images, NIR images and optical images of a specimen, the system comprising:
  a cabinet defining an interior chamber and an equipment enclosure;
  a display;
  an x-ray system including:
    an x-ray source positioned in the interior chamber;
    an x-ray detector positioned in the interior chamber;
    a specimen platform positioned in the interior chamber and which is a protective cover of and in physical contact with the x-ray detector; and
    a motion control mechanism positioned in the interior chamber and configured for moving the x-ray source to or along a plurality of positions within the interior chamber relative to the specimen disposed on the specimen platform;
  an optical camera positioned in the interior chamber configured to capture an optical image of the specimen;
  an NIR image system configured to capture an NIR image of the specimen, the NIR image system including:
    an NIR camera/detector; and
    an NIR excitation light; and
  a controller positioned in the equipment enclosure and configured to:
    selectively energize the x-ray source to emit x-rays through the specimen to the x-ray detector at selected positions of the x-ray source relative to the specimen such that the isocenter of the emitted x-rays at the selected positions is located at a surface of the x-ray detector;
    control the x-ray detector to collect projection x-ray images of the specimen when the x-ray source is energized at the selected positions, wherein one of the projection x-ray images is a two-dimensional x-ray image taken at standard imaging angle of approximately 0°;
    create a tomosynthetic x-ray image reconstructed from a collection of projection x-ray images;
    process the collection of the projection x-ray images in the controller into one or more reconstructed tomosynthetic x-ray images representing a volume of the specimen and relating to one or more image planes that are selectively the same or different from that of the two-dimensional x-ray image;
    control the optical camera to capture and collect the optical image of the specimen;
    control the NIR image system to capture and collect the NIR image of the specimen; and
    selectively display the NIR image and at least one of the two-dimensional x-ray image, the one or more reconstructed tomosynthetic x-ray images and the optical image on the display.

11. The cabinet x-ray, NIR and optical camera system of claim 10, wherein the cabinet comprises a walled enclosure surrounding the interior chamber, a door configured to cover the interior chamber and a sampling chamber within the interior chamber for containing the specimen.

12. The cabinet x-ray, NIR and optical camera system of claim 10, wherein the specimen platform is configured for excised tissue, organ or bone specimens.

13. The cabinet x-ray, NIR and optical camera system of claim 10, wherein the specimen platform is configured for any organic or inorganic specimen that fits inside an x-ray cabinet.

14. The cabinet x-ray, NIR and optical camera system of claim 10, wherein the controller is configured to control the x-ray detector to collect projection x-ray images of the specimen when the x-ray source is energized and control the NIR system to capture and collect the NIR image of the specimen such that the NIR image is collected at substantially the same time as at least one of the projection x-ray images.

15. The cabinet x-ray, NIR and optical camera system of claim 10, wherein the orientation of the specimen in the two-dimensional x-ray image, the one or more reconstructed tomosynthetic x-ray images, the NIR image and the optical image are substantially the same.

16. The cabinet x-ray, NIR and optical camera of claim 11, wherein the NIR image system is within the walled enclosure.

17. The cabinet x-ray, NIR and optical camera of claim 11, wherein the NIR image system is external to the walled enclosure.

* * * * *